United States Patent
Larson

(10) Patent No.: US 10,105,702 B2
(45) Date of Patent: Oct. 23, 2018

(54) MICROFLUIDIC METHODS FOR MANIPULATING DNA

(71) Applicant: Lariat Biosciences, Inc., Beverly, MA (US)

(72) Inventor: Jonathan W. Larson, Chelsea, MA (US)

(73) Assignee: Lariat Biosciences, Inc., Beverly, MA (US)

( * ) Notice: Subject to any disclaimer, the term of this patent is extended or adjusted under 35 U.S.C. 154(b) by 102 days.

(21) Appl. No.: 14/777,203

(22) PCT Filed: Mar. 17, 2014

(86) PCT No.: PCT/US2014/030346
§ 371 (c)(1),
(2) Date: Sep. 15, 2015

(87) PCT Pub. No.: WO2014/145555
PCT Pub. Date: Sep. 18, 2014

(65) Prior Publication Data
US 2016/0136643 A1    May 19, 2016

Related U.S. Application Data

(60) Provisional application No. 61/792,310, filed on Mar. 15, 2013, provisional application No. 61/804,326, (Continued)

(51) Int. Cl.
*C12Q 1/68*    (2018.01)
*B01L 3/00*    (2006.01)
(Continued)

(52) U.S. Cl.
CPC ...... *B01L 3/502784* (2013.01); *B01F 5/0647* (2013.01); *B01F 13/0071* (2013.01);
(Continued)

(58) Field of Classification Search
None
See application file for complete search history.

(56) References Cited

U.S. PATENT DOCUMENTS

| | | | |
|---|---|---|---|
| 2002/0058332 A1* | 5/2002 | Quake | ............... B01L 3/502761 435/288.5 |
| 2008/0014589 A1 | 1/2008 | Link et al. | |

(Continued)

FOREIGN PATENT DOCUMENTS

| | | |
|---|---|---|
| WO | WO-2008063227 A2 | 5/2008 |
| WO | WO-2011028539 A1 | 3/2011 |

(Continued)

OTHER PUBLICATIONS

International Search Report completed on Aug. 4, 2014 for PCT/US2014/030346.

(Continued)

*Primary Examiner* — Betty J Forman
(74) *Attorney, Agent, or Firm* — Foley Hoag LLP

(57) ABSTRACT

Techniques are provided for generating, manipulating, and measuring fluidic droplets in mixed phase systems based on establishing transient continuities between otherwise spatially separated phases. In certain methods of the invention, electrodes in contact with the continuous phases allow electrical monitoring of continuity or proximity of separated phases as a means to characterize droplets. In other methods of the invention, fluidic continuity provides a means for generating droplets, injecting or extracting the contents of droplets, and sorting droplets. Chemical techniques are also provided that use these droplet-based methods, or others, to quantify and identify nucleic acids through incorporation into hydrogel particles. The nucleic acids are entrapped either actively by chemical incorporation during gel polymerization or passively by chain entanglement. After incorporation into the hydrogel particles, the nucleic acids are (Continued)

solvent accessible either at the particle periphery or within internal pores for further biochemical manipulations and characterization. In one important aspect, the invention combines the high specificity, high sensitivity, and unbiased performance of clonal DNA amplification in free solution with the simplicity of permanently co-localizing the separate reaction products onto rigid substrates for myriad biochemical applications.

54 Claims, 17 Drawing Sheets

Specification includes a Sequence Listing.

Related U.S. Application Data filed on Mar. 22, 2013, provisional application No. 61/808,980, filed on Apr. 5, 2013, provisional application No. 61/834,005, filed on Jun. 12, 2013.

(51) Int. Cl.
| | |
|---|---|
| *B01F 5/06* | (2006.01) |
| *B01F 13/00* | (2006.01) |
| *C12Q 1/6816* | (2018.01) |
| *C12Q 1/6844* | (2018.01) |
| *C12Q 1/686* | (2018.01) |
| *G01N 27/447* | (2006.01) |

(52) U.S. Cl.
CPC ........ *B01L 3/502715* (2013.01); *C12Q 1/686* (2013.01); *C12Q 1/6816* (2013.01); *C12Q 1/6844* (2013.01); *G01N 27/44791* (2013.01); B01L 2200/10 (2013.01); B01L 2300/0663 (2013.01); B01L 2300/0864 (2013.01); B01L 2400/0415 (2013.01)

(56) References Cited

U.S. PATENT DOCUMENTS

| | | |
|---|---|---|
| 2010/0136544 A1 | 6/2010 | Agresti et al. |
| 2011/0053798 A1* | 3/2011 | Hindson .............. C12Q 1/6844 506/12 |
| 2012/0309002 A1* | 12/2012 | Link .................. C12N 15/1068 435/6.11 |
| 2016/0045914 A1* | 2/2016 | Abate ................. B01F 13/0071 137/1 |

FOREIGN PATENT DOCUMENTS

| | | |
|---|---|---|
| WO | WO-2011/100604 A2 | 8/2011 |
| WO | WO-2012/135259 A1 | 10/2012 |

OTHER PUBLICATIONS

Supplementary European Search Report completed on Oct. 10, 2016 for EP 14 76 5235.

* cited by examiner

Fig. 23

MICROFLUIDIC METHODS FOR MANIPULATING DNA

CROSS-REFERENCE TO RELATED APPLICATIONS

This application is the U.S. National Stage of international application no. PCT/US2014/030346, filed Mar. 17, 2014, which claims the benefit of and priority to U.S. Provisional Application Ser. No. 61/792,310, filed Mar. 15, 2013, 61/804,326, filed Mar. 22, 2013, 61/808,980, filed Apr. 5, 2013, and 61/834,005, filed Jun. 12, 2013, all of which are hereby incorporated herein by reference in their entirety.

The instant application contains a Sequence Listing which has been submitted electronically in ASCII format and is hereby incorporated by reference in its entirety. Said ASCII copy, created on Nov. 11, 2015, is named LAR_00101_Sequence_Listing.txt and is 1,107 bytes in size.

BACKGROUND

Droplet-based microfluidic techniques have led to numerous high profile commercial applications in biotechnology, including DNA sequencing, genomic enrichment for sequencing, and digital PCR. Novel biochemical methods are provided herein to overcome significant limitations in these applications. Novel microfluidic methods are provided that are best suited to support the biochemical methods of the invention, and yet also offer substantial improvements for any droplet-based microfluidic application.

In the field, successful implementation of droplet-based techniques has generally required expensive vision systems to orchestrate automated priming and operation of microfluidic circuitry. Tasks shouldered by vision systems typically include filling channels with fluids, measuring droplet sizes during generation, and characterizing the mixing of droplets either with other droplets or with continuous phases. Typically the results are fed back as a part of closed-loop instrument control. Described herein are non-optical methods for performing the same fluidic tasks, greatly reducing the cost and complexity of droplet-based microfluidics.

In brief description, in some aspects the invention is a method for detecting droplets; in other aspects it is a method for generating droplets; in other aspects it is a method for manipulating the contents of droplets; and in yet other aspects it is a method for sorting the contents of droplets. In one embodiment, the invention is a microfluidic circuit comprising four channels meeting at an intersection, such as an 'X' shape. Two opposing channels carry continuous phases of aqueous liquid, called the side channels herein, and a third channel—perpendicular to the previous two and called the main channel herein—carries a stream of aqueous droplets into the intersection flowing within a continuous phase of oil. The oil from the main channel phase separates from the aqueous fluids in the side channels producing an oil gap between the aqueous phases in the intersection. The fourth channel is an outlet. Pressure is applied to the side channels, driving their contents into the intersection and contacting individual droplets arriving from the main channel. The fluidic system is poised such that when a droplet arrives from the main channel, it contacts the boluses of fluid emerging from the side channels and merges with them, forming a transient aqueous bridge from one side channel to the other. During this time, some fluid may flow between the droplet and the side channels, changing the contents of the droplet before it is sheared off in flow as it emerges into the outlet channel.

Electrodes are positioned in direct electrical contact with the fluid in the side channels, at least one per channel, and a voltage is applied across the electrodes. The electrical circuit is an open circuit before the arrival of a droplet because the oil-filled intersection is electrically insulating, hence no electrical current flows. On the arrival of a droplet an aqueous bridge forms, closing the electrical circuit allowing current to flow during the excursion of the droplet through the intersection. Once the droplet snaps off after its excursion through the intersection, the oil breaks the electrical circuit again and the current stops until the arrival of the next droplet. In this manner, bursts of electrical current provide a direct observation of droplets that can be used for typical droplet characterizations such as counting droplets and measuring droplet volume.

Additionally, the relative pressures within the droplets and the side channels can be poised allowing flow into or out of the droplets, providing another key feature of a droplet-based fluidic system: the ability to mix reagents. Furthermore, in certain embodiments of the invention the merging of droplets with the continuous phases requires the application of a voltage, such as with surfactant stabilized interfaces. In this method of the invention, the voltage can be pulsed selectively depending on a trigger signature, such as a burst of fluorescence from a sample contained in a droplet, to capture the contents of selected droplets in the side channels or to selectively add reagents to particular droplets. Lastly, the device may be operated as a droplet generator by merging the fluids from the side channels directly without the assistance of a stream of droplets from the main channel. In these methods of the invention, as the boluses of liquid from the side channels make direct contact inside the fluidic intersection, they merge creating a detectable closed electrical circuit before a newly generated droplet snaps off. Thus methods of the invention are provided for generating, mixing, sorting, and measuring droplets, the key aspects of any droplet-based microfluidic system.

Techniques for merging droplets have been disclosed in, for example, U.S. patent application Ser. No. 13/379,782, filed Jun. 25, 2010, entitled "Fluid Injection", by Weitz et al., published as U.S. Patent Application Publication No. 2012/0132288 on May 31, 2012, that describes a device called the "picoinjector". The picoinjector consists of a T-junction, or a series of T-junctions, with each T-junction unit consisting of a single continuous phase channel, called the side channel on the stem of the 'T', and a main channel across the top of the 'T'. The pressure of the continuous phase in the picoinjector is poised such that a bolus of liquid extends partially into the fluidic intersection until flow stops from opposition by the Laplace pressure that grows as the bolus protrudes further into the intersection. A stream of droplets in oil flows in the main channel into the intersection, but the droplets do not merge with the protruding continuous phase unless assisted by a high voltage electrical field from nearby electrodes. Once the electrical field is applied, the thin surfactant-stabilized membrane between the amplified droplets and the continuous aqueous phase ruptures allowing flow of the continuous phase into the droplet. After the emerging bolus of combined liquid from the droplet and the flowing continuous phase reaches a critical volume, the bolus snaps off from the continuous phase due to fluidic shearing. As long as the snap occurs before the arrival of the next droplet, the operation succeeds in adding a fixed volume from the continuous phase into each droplet. Also the picoinjector can be run in reverse, extracting the contents of droplets into the side channel for sorting and other applications.

Techniques for merging droplets have also been disclosed in U.S. patent application Ser. No. 13/371,222, filed Feb. 10, 2012, entitled "Methods for Forming Mixed Dropets", by Yurkovetsky et al., published as U.S. Patent Application Publication No. 2012/0219947 on Aug. 30, 2012, that describes a device called the "lambda-injector" because the stem of the 'T' is typically bent away from a right angle. The microfluidic device operates similarly to the picoinjector except the pressure of the continuous phase is increased such that the stable interface between the continuous aqueous phase and the oil is broken. Rather, the continuous phase protrudes far enough into the intersection such that it is repeatedly sheared into discrete droplets, similar to simple droplet generation in a T-junction described by Thorsen et al. (see *Phys. Rev. Lett.* 86(18), 4163-4166, 2001). However in this method the frequency of droplet generation is set lower than the arrival frequency of a stream of droplets across the top of the 'T'. Hence the droplets arrive at the intersection before the snap of the continuous phase occurs, and they merge with the emerging bolus of continuous phase under the influence of the high voltage electrical field. The new enlarged bolus snaps off immediately.

Techniques for merging droplets have also been disclosed in International Patent Application. No. PCT/US2012/030811, filed Mar. 28, 2012, entitled "Injection of Multiple Volumes Into or Out of Droplets", by Abate et al., Published as International Publication No. WO 2012/135259 on Oct. 4, 2012, that describes the use of multiple picoinjectors sequentially or simultaneously to inject multiple controlled volumes into an incoming stream of droplets. While pico- and lambda-injectors have traditionally employed solid electrodes in contact with the fluid intersection, O'Donovan et al. described a different picoinjector that has one electrode in fluidic contact with a side channel and another in fluidic contact with an electrically isolated "faraday mote" (see *Lab Chip* 12, 4029-4032, 2012).

All of the embodiments of the pico- and lambda-injectors described above have one common trait: disrupting fluidic interfaces by electrical methods is performed by applying a high voltage electrical field through one or more electrically isolated electrodes. In all cases except for one, the electrical field is supplied by a pair of electrodes in close proximity to the merge zone. The one exception, the device from O'Donovan et al. (2012), employs just one proximal fluid electrode, the "faraday mote". However even in this device it is a high voltage electrical field that is applied to the interface through electrically isolated electrodes. Due to the electrical isolation between the electrodes, none of the aforementioned techniques are capable of carrying a steady and substantial electrical current that reveals droplet dynamics within the device. In contrast, one core of the invention here is that electrical current, not an electrical field, is applied to the interface through external electrodes in fluid contact with the injection channels. Charge accumulation destabilizes the interfaces allowing fluids to merge. Droplet dynamics within the microfluidic device are readily observed and interpreted through perturbations of the electrical current.

Other aspects of the invention include applications of the microfluidic methods described above, or other fluidic methods, for molecular quantitation in general but especially for DNA quantitation. DNA quantitation by polymerase chain reaction (PCR) amplification is an almost universal technique in molecular biology with countless applications. Conventional quantitative PCR (qPCR) is performed by monitoring the reaction product after each thermal cycle during amplification, typically detecting a fluorescence signal that is proportional to the DNA concentration. qPCR measurements are relatively precise within around a factor of two, and when compared against a standard curve they can be accurate to that extent as well (see Baker et al., *Nature Methods*, 9(6), 541-544, 2012). qPCR reactions can also be multiplexed (quantifying multiple targets within the same reaction mixture) using separate sequence-specific probes that fluoresce at different wavelengths. However qPCR has critical limitations for certain applications. For example, multiplexing qPCR is generally limited to five or fewer reactions due in part to the constrained spectral space but also more importantly to the serious challenge of compatibility between reactions. Hence in practice qPCR is seldom multiplexed. Another important limitation of qPCR is sensitivity for rare genetic variants amidst a large background of wild-type DNA, with sensitivities rarely exceeding 1:100 mutant-to-wild-type ratios (M-Wt) (see Baker et al., above). qPCR is also susceptible to cross-contamination of samples with amplified DNA from previous runs due to the vast amounts of reaction products, called amplicons, generated by amplification.

Digital PCR (dPCR) is a technique that improves on many of the shortcomings of qPCR, and it is based on diluting and dividing a sample into small enough volumes such that each volume is likely to contain either zero or one target DNA molecule, called a limiting dilution (see Sykes et al., *Biotechniques*, 13(3), 444-449, 1992). In dPCR, amplification reactions are run to the end-point and the number of PCR(+) reactions, indicated by bright fluorescence signals, are compared to the number of PCR(−) reactions, indicated by low fluorescence signals, as a direct measurement of the starting DNA concentration. Using an emulsion format for dPCR, where millions of individual PCR reactions are isolated within neighboring microfluidic droplets approximately 10 pL in volume, extremely high sensitivities exceeding $1:10^5$ M-Wt have been achieved with dPCR (for example, see Pekin et al., *Lab Chip*, 11, 2156-2166, 2011). Such high sensitivity is enabled by the isolated environment surrounding the mutant molecules: mutant amplification does not compete with the wild-type in dPCR as it otherwise does in bulk reactions with qPCR. Digital PCR also benefits in a different manner from single target encapsulation. Multiplexed reactions are quite simple to develop because the different reactions never compete. At limiting dilution, only one PCR reaction within each droplet actually initiates even though the reaction mixture contains PCR primers for all of the multiplexed reactions. This biochemical simplification enabled Zhong et al. to demonstrate a 9-plex reaction with little more development than a single-plex reaction (Zhong et al., *Lab Chip*, 11, 2167-2174, 2011). Furthermore, dPCR also allows separate reactions in a multiplexed mixture to be identified by fluorescence intensity as well as color, enabling the discrimination of the 9-plex reaction that would otherwise have been impossible by conventional qPCR considering the spectral limitations of commonly used fluorophores.

Emulsion dPCR is a powerful method for "needle in a haystack" type applications, and it offers significantly greater potential for multiplexing than standard qPCR. However a tradeoff exists between sensitivity and plexity with this approach. Since droplets are discriminated in part by fluorescence intensity, false positive droplets for one reaction that can normally be identified as outliers based on aberrant intensity may erroneously appear as true positive reactions of a different type. For this reason, the number of different targets is often limited to four or fewer while still not achieving the full sensitivity of single-plex reactions.

Emulsion dPCR also presents a carry-over contamination risk. In conventional qPCR carry-over is derisked by sealing the PCR reaction into tubes and plates before thermal cycling, and then the signal is read out afterwards without ever re-opening the container. In contrast, in dPCR the emulsion is typically removed from standard PCR labware after thermal cycling to perform readout on custom instrumentation. Maintaining an unbroken seal on the amplicons requires either custom integration of thermal cycling with serial one-by-one readout of the droplets, or else a mechanical solution is required to contain the amplicons permanently during and after transfer to the reader. Both approaches are costly and awkward.

Aspects of the invention involve solutions to both of the above issues clouding emulsion dPCR. As is described in detail below, the invented method involves encapsulating the nucleic acid sample at limiting dilution in an emulsion and then amplifying the sample. The microfluidic methods of the invention are ideally suited for then entrapping the amplified reaction products (amplicons) within individual hydrogel particles. The DNA from each droplet is sequestered into hydrogel microparticles such that each microgel contains the DNA from one and only one original droplet. In this manner the physical containment of the amplicons shifts from the emulsion format to a solid support. The invented method provides a layer of defense against carry-over contamination by physically immobilizing the amplicons within particles, and it circumvents the limitations on multiplexing in conventional emulsion dPCR by liberating the amplicons from the confined environment of droplets. For example, the amplicons can be washed and probed by hybridization once they are embedded in particles, whereas even this simple procedure is unmanageable for amplicons in an emulsion. With regard to DNA entrapment the invention is not limited to the microfluidic methods of the invention. However the microfluidic methods of the invention are preferred for the biochemical methods of the invention.

One digital PCR technique that is related to the invention is called BEAMing (see Diehl et al., *Nature Methods*, 3(7), 551-559, 2006). In this approach the target sample is emulsified after bulk pre-amplification into small aqueous droplets ~10 μm in diameter within an oil carrier solution. The emulsified solution also contains small 1 μm diameter magnetic beads coated with oligonucleotides that are complementary to universal sequences incorporated into the amplicons during pre-amplification. A second round of emulsion PCR extends the bead-bound oligos into entire amplicons. Post-PCR the emulsion is broken, the beads are washed, and then the amplicon-coated beads are probed by sequence-specific hybridization with fluorescent oligonucleotide probes. The beads are read-out using a standard flow cytometer, and the number of fluorescent beads counted corresponds to the initial target concentration.

BEAMing shares a common advantage with the invention: the amplicons are captured on a solid support after emulsion PCR, facilitating downstream analysis with conventional tools for biochemical characterization. However, BEAMing is fundamentally different from the invention in that the droplets in BEAMing contain zero, one, or more beads for solid support. In contrast, in the invention the droplets themselves become the solid support through polymerization, guaranteeing that the contents of each droplet are captured into a particle. Also, in BEAMing bulk pre-amplification is required to incorporate universal tags prior to emulsion PCR, whereas no pre-amplification is required in the invention. These differences translate into numerous important functional advantages for the invention.

In BEAMing, the number of beads per droplet is dictated by a probability distribution. If the droplets are all equally sized, the bead occupancy follows the Poisson distribution. Diehl, et al. (2006) teach that fewer than 20% of the droplets should contain multiple beads, a relatively low bead concentration that results in over 40% of the droplets containing zero beads according to the Poisson distribution. Any template DNA is wasted in droplets without beads, a serious shortcoming for applications requiring high sensitivity. However, it can be difficult to achieve uniform droplet volumes with methods that are also compatible with beads. The highest droplet uniformities that have been reported were achieved by microfluidic techniques, however microfluidic droplet generators are very susceptible to clogging by beads. Instead, emulsification in BEAMing is generally performed by mechanical agitation, resulting in droplets with ~10-fold variation in diameter, corresponding to ~1000-fold variation in volume. Such high non-uniformity results in further waste of template if the guideline of 20% maximum occupancy is applied to the largest droplets. This non-uniformity can also pose other challenges related to the wide variation in reaction conditions. For example, PCR may saturate earlier in smaller droplets where the amplicon concentration rises more quickly due to increased confinement. At a limiting dilution, the number of amplicons inside each PCR-positive droplet is always similar during the exponential stage of PCR regardless of droplet size. Consequently the amplicon concentration in the smaller droplets will be larger, resulting in earlier onset of PCR saturation and hence lower overall yield of amplicons. In contrast, droplets in the invention may be very uniformly sized yielding highly uniform reaction conditions. Also, the contents of each droplet in the invention are counted for maximum assay sensitivity.

Pre-amplification is another shortcoming of BEAMing that is avoided by the invention. There are two significant problems with pre-amplification. First, in SNP genotyping assays (an important application for dPCR) the assay must distinguish the difference of a single base pair along a ~100 bp strand, however during pre-amplification two almost complementary strands from the different alleles can nevertheless still hybridize together resulting in ambiguous or misleading results after emulsion PCR. While thermodynamics favors the perfect match between complementary strands, the specificity of amplicon hybridization is often dictated by non-equilibrium binding kinetics. In other words, the mismatch might not be energetically perfect, but on the time scale of the reaction if the first encounter between two strands is a mismatch, the complex may not dissociate again before entrapment into the emulsion. Furthermore, higher M-Wt ratios increase the probability of mismatches, effectively reducing the number of properly matched mutant amplicons for analysis. Since it is generally standard procedure in BEAMing to disregard beads that contain signal from both alleles, the outcome is reduced sensitivity.

The second issue with pre-amplification is the loss of sensitivity due to polymerase error. DNA polymerases without proof-reading functions mis-incorporate nucleotides at a rate of about 1 in 10,000 base pairs (reviewed by Cha and Thilly, 1993), imposing a fundamental limit on the sensitivity of the assay. In essence, the polymerase creates mutants from the wild-type that are indistinguishable from true mutant-types. Emulsion PCR without pre-amplification overcomes this fundamental limitation by detecting the mixture of wild-type and mutant amplicons that arises from mis-incorporation. Only true mutants yield mutant-only PCR(+) droplets.

In summary, due to the combination of non-uniform emulsions, pre-amplification, and polymerase error, BEAMing is limited to a sensitivity of about 1:10,000 M-Wt, a capability that is 10-100 times lower than achievable by dPCR, the basis of the invention. Furthermore, BEAMing is poorly suited to multiplexing applications because pre-amplification is widely known to introduce unpredictable bias in reaction yield among the different competing reactions. Aspects of the invention avoid all of these shortcomings.

Techniques for encapsulating biomolecules microgels have been disclosed in, for example, International Patent Application No. PCT/CA2005/000627, filed Apr. 25, 2005, entitled "Method of Producing Polymeric Particles with Selected Size, Shape, Morphology and Composition", by Kumacheva et al., published as U.S. Patent Publication No. 2011/0129941 on Jun. 2, 2011 that describes methods for capturing DNA within hydrogel particles formed from emulsions in which the individual droplets are hardened into particles of pre-determined shapes that are dictated by confinement into microfluidic channels, including spherical shapes. The particles emerge from the microfluidic device rigidified into their final shape. While certain methods of the invention do envision performing some degree of pre-polymerization of droplets within microfluidic channels to stabilize the emulsion, no requirement exists to rigidify the droplets by gelation within a microfluidic device into any particular shape, nor does the invention have a requirement for microfluidic approaches at all. And, while not limited in this regard, spherical particles formed spontaneously by droplets in bulk emulsion are preferred for simplicity in the invented method.

Techniques for confining and synthesizing DNA within microgels have also been disclosed, for example in International Patent Application No. PCT/US08/03185, filed Mar. 7, 2008, entitled "Assays and Other Reactions Involving Droplets", by Agresti et al., published as U.S. Patent Publication No. 2010/0136544 on Jun. 3, 2010 that describes amplifying individual DNA molecules within gel droplets, fabricated by polymerizing an emulsion containing DNA at limiting dilution, and where one of the PCR primers is covalently incorporated into the gel before amplification. The spatially co-localized clonal amplicons are termed a "polony", for polymerase colony, and they can be washed, treated, and analyzed similarly to the gel-incorporated amplicons of the invention. However, the similarity in outcome is superficial since the process for fabrication of gel-incorporated clonal amplicons is different for polonies compared to those of the invention. In the method of Agresti et al. (2006) PCR amplification proceeds by extending primers already bound to a pre-formed gel matrix, whereas in the methods of the invention the primers are unbound during amplification and the gel matrix is formed after DNA amplification. One strong advantage of solution-state DNA amplification is PCR efficiency. Diffusion is impeded in the confined environment of pores inside of hydrogels in the method of Agresti et al., with numerous potential pitfalls. First, hindered amplicon diffusion leads to locally high amplicon concentrations, potentially causing early PCR saturation due to amplicon-amplicon interactions competing with primer hybridization and also non-uniform particle loading with amplicons. Second, hindered diffusion of the reverse primer leads to its local depletion, exacerbating the issues above. Third, the forward primer, being bound, cannot diffuse at all. Hence the reaction depends on the diffusion of both the target DNA and the amplicons causing the reaction kinetics to be sluggish especially in the first few replications. Some of the initial template DNA molecules, generally being significantly larger than the amplicons, may also become immobilized during gel polymerization thus preventing any amplification from initiating and resulting in an overall loss in sensitivity. Additionally, the locally high concentrations of DNA and primers caused by confinement increase the opportunity for amplification of non-specific genomic DNA fragments or primer-primer products. Some of these concerns for polonies can be mitigated by increasing the pore size of the particles, however large pore sizes may reduce the efficiency of incorporating amplicons into the gel. Due to such biochemical and other limitations (see Edwards, Jeremy S. "Polony Sequencing: History, Technology, and Applications." Ed. Michal Janitz. *Next-Generation Genome Sequencing: Towards Personalized Medicine.* John Wiley & Sons, 2011), the original polony concept (see Mitra and Church, *Nucleic Acids Res.,* 27(24), e34, 1999) actually adopted aspects of BEAMing during its evolution into polony sequencing (see Shendure et al., *Science,* 309, 1728-1732, 2005). The issues of incorporation efficiency and non-ideal PCR conditions are overcome by methods of the invention.

SUMMARY

Some methods can include providing a system, the system including a substrate that defines microfluidic channels including a main channel having a main input in fluid communication with a main output, the main channel defining an intersection site along a path of fluid flow from the main input to the main output, a first side channel having a first side input in fluid communication with a first side output, the first side output being in fluid communication with the main channel at the intersection site, a second side channel having a second side input in fluid communication a second side output, the second side output being in fluid communication with the main channel at the intersection site, a first electrode located so as to be in electrical contact with the first side channel fluid when the first side channel has been charged with the first side channel fluid, a second electrode located so as to be in electrical contact with the second side channel fluid when the second side channel has been charged with the second side channel fluid. Such methods can further include charging the main channel with a main channel fluid from the main input, charging the first side channel with a first side channel fluid from the first side input, the first side channel fluid being immiscible with at least a first component of the main channel fluid, charging the second side channel with a second side channel fluid from the second side input such that the first and second side channels are separated from one another by the main channel fluid, the second side channel fluid being immiscible with at least the first component of the main channel fluid, flowing the main channel fluid from the main channel input to the main channel output and through the intersection point, connecting the first and second side channel fluids with a fluid bridge at the intersection point, and disconnecting the fluid bridge from at least one of either the first or the second side channel fluids so that the first and second side channel fluids are separated by the first component of the main channel fluid.

In such methods the fluid bridge can consist of a second component of the main channel fluid.

In such methods, the first and second side channel fluids can be miscible with each other.

In such methods, the fluid bridge can be miscible with both the first and second side channel fluids.

In such methods, connecting the first and second side channel fluids with the fluid bridge can include forming an electrically conductive connection between the first and second side channel fluids.

In such methods, the system can further include a voltage source connected to both the first electrode and the second electrode.

In such methods, the first electrode can be located within the first side channel, and the second electrode can be located within the second side channel.

In such methods, the first side channel fluid, the second side channel fluid and the fluid bridge can all be aqueous.

In such methods, the first component of the main channel fluid can be an oil.

In such methods, the fluid bridge can consist essentially of the first and second side channel fluids, and can contain substantially none of the first component of the main channel fluid.

In such methods, connecting the first and second side channel fluids with a fluid bridge can include extending the first and second side channel fluids into the intersection site so that the first and second fluids come into contact, thereby forming the fluid bridge.

In such methods, disconnecting the fluid bridge from the first and second side channel fluids can include separating the fluid bridge from both the first and second side channel fluids thereby creating a droplet consisting essentially of the first and second side channel fluids.

In such methods, the disconnected fluid bridge can include a species and reactants for gel polymerization, the method further comprising entrapping the species within a gel in the droplet by gel polymerization of the reactants. The species can be, for example, (a) a nucleic acid, or (b) a cell.

In such methods, the system can further include a current meter operably connected to the first and second electrodes so as to be capable of measuring the current between the first and second electrodes as a function of time. Such methods can include recording the current measured by the current meter as a function of time.

In such methods, the fluid bridge can be miscible with the first side channel fluid, or the second side channel fluid, or both.

In such methods, the fluid bridge can be immiscible with the first side channel fluid.

In such methods, the fluid bridge can be immiscible with the second side channel fluid.

In such methods, the fluid bridge can be a second component of the main channel fluid; and flowing the main channel fluid comprises flowing the fluid bridge from the main channel input to the intersection point and from the intersection point to the main channel output.

In such methods, the system can further include a current meter operably connected to the first and second electrodes so as to be capable of measuring the current between the first and second electrodes as a function of time, and the method can further comprise recording the current measured by the current meter as a function of time.

In such methods, connecting the first and second side channel fluids with the fluid bridge can include incorporating at least some of the first and/or second side channel fluids into the fluid bridge, and disconnecting the fluid bridge can include retaining in the fluid bridge the incorporated at least some of the first and/or second side channel fluids.

In such methods, disconnecting the fluid bridge can include disconnecting the fluid bridge from the second side channel fluid, and maintaining contact between the fluid bridge and the first side channel fluid.

Such methods can include flowing the fluid bridge from the main channel into the first side channel.

In such methods, the system can further include a first pressure source in fluid communication with the first side input, the first pressure source configured so that if the first side channel is charged with a first side fluid, the first pressure source is capable of generating or maintaining within the first side channel fluid a positive pressure, or a negative pressure, or zero pressure with respect to the pressure of the main channel fluid at the intersection site, and a second pressure source in fluid communication with the second side input, the second pressure source configured so that if the second side channel is charged with a second side fluid, the second pressure source is capable of generating or maintaining within the second side channel fluid a positive pressure, or a negative pressure, or zero pressure with respect to the pressure of the main channel fluid at the intersection site.

In such methods, the second side channel can define (a) a second side current channel and (b) a second side pressure channel, the second side current channel and the second side pressure channel both be in fluid communication with the input port, the second side current channel and the second side pressure channel can be contiguous at a second side intersection point in the second side channel, the second side electrode can be positioned within the second side current channel and the second pressure source can be positioned in the second side pressure channel.

In such methods, the fluid flow path from the second side intersection point to the second side electrode can be substantially different in length, cross-sectional area, or both length and cross-sectional area than the fluid flow path from the second side intersection point to the second pressure source.

In such methods, the fluid flow path from the second side intersection point to the second side electrode can be substantially similar to the fluid flow path from the second side intersection point to the second pressure source.

In such methods, the second side channel can include a third side input in fluid communication with the second side output.

Such methods can include charging the second side channel with a third side channel fluid from the third side input.

In such methods, the first side channel fluid can include a bead attached to a hybridization capture agent complementary to a predetermined nucleic acid sequence.

Some methods of containing a species can include encapsulating the species within a fluid droplet, then injecting into the fluid droplet reactants for gel polymerization, then rigidifying the droplet by gel polymerization, and then capturing the species within the rigidified droplet during polymerization.

In such methods, injecting can include a method according to any of the injection methods disclosed herein.

In such methods, injecting can include microfluidic injection, picoinjection or lambda injection.

In such methods, the species can include a nucleic acid and the nucleic acid can be clonal, or, for example, the species can include a cell.

In such methods, the clonal nucleic acid can arise from encapsulating a single DNA molecule within a droplet, and then amplifying the DNA within the droplet.

Such methods can include characterizing the nucleic acid.

In such methods, characterizing can include sequencing the nucleic acid.

Such methods can include identifying and quantifying genotypes based on the characterization of the nucleic acid.

Such methods can include sorting the rigidified droplet based on the characterization of the nucleic acid.

Such methods can include characterizing the sorted droplets.

Such methods can include characterizing the sorted droplets comprises sequencing the nucleic acid.

Such methods can include identifying and quantifying genotypes based on the characterization of the nucleic acid.

In such methods, the nucleic acid can be DNA arising from amplification with one or more primers containing a functional group for covalent incorporation into the gel matrix via free radical chemistry during gel polymerization.

In such methods, the functional group is a 5' acrydite.

In such methods, the nucleic acid can be DNA amplified with one or more primers that either leave an overhang after DNA extension or are cleaved into an overhang.

In such methods, the primer can include a target binding region and an overhang region, and where the overhang region comprises nucleic acid analogs.

In such methods, the nucleic acid analogs can be LNAs or PNAs.

In such methods, the DNA can be amplified with one or more tripartite primers comprising a 3' target binding region, a 5' attachment region that forms an overhang during polymerization, and a non-replicable region in between that blocks the polymerase from extending the overhang.

In such methods, the DNA can concatemerize at room temperature, with or without unions and blocks, and with or without restriction digestion and ligation, entrapping the DNA within the gel droplet.

A method of co-localizing clonal DNA can include injecting into a droplet a bead attached to a hybridization capture agent complementary to a predetermined nucleic acid sequence, the droplet containing amplified DNA, and capturing the amplified DNA to the hybridization capture agent.

In such methods, injection can include any of the injection methods herein.

Such methods can include characterizing the captured DNA.

In such methods, characterizing can include sequencing the DNA.

Such methods can include identifying and quantifying genotypes based on the characterization of the nucleic acid.

A kit for genotyping variable DNA sequences can include a first hybridization probe complementary to a first predetermined sequence and a second hybridization probe complementary to a second predetermined sequence. The first predetermined sequence can be a wild-type sequence of a conserved domain and the second predetermined sequence can be a wild-type sequence including a suspected variable domain. The first and second probes can each have different, independently detectable signatures.

In some such kits, the detectable signatures of the first and second probe are selected from the following group: radioactive labeling, absorbence, phosphorescence, chemiluminescence, and fluorescence.

Methods of genotyping variable DNA sequences can include providing a kit for genotyping variable DNA as described above, providing target nucleic acids, hybridizing the first and second probes to the target nucleic acids, determining the presence or absence the detectable signature of each of the first and second probes, inferring (a) the presence of the wild type DNA if both detectable signatures are detected, or (b) the presence of a mutation if only the detectable signature of the first probe is detected.

Such methods can include sequencing the DNA in order to identify the mutation if the presence of a mutation has been inferred.

BRIEF DESCRIPTION OF THE DRAWINGS

FIG. 23 shows a DNA genotyping assay.

DETAILED DESCRIPTION

Figure 1:
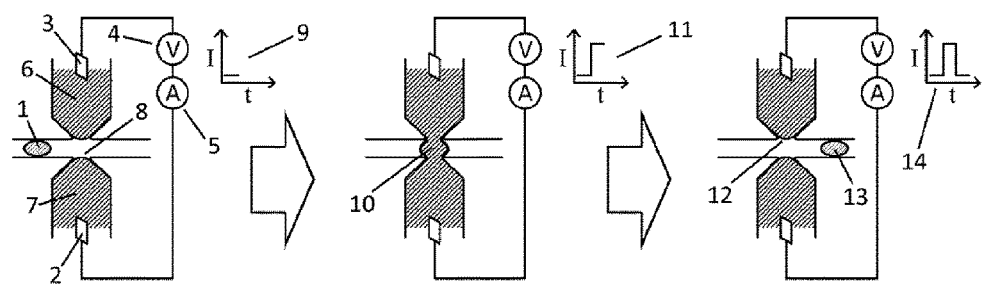
FIG. 1 shows electrical detection of a droplet.

Aspects of the invention encompass methods for creating, manipulating, and characterizing droplets. Other aspects of the invention also include a microfluidic apparatus that creates, manipulates, and/or characterizes droplets. The microfluidic method and/or apparatus may be specialized for a specific one of these functions, or it may be general enabling some or all of the functions. Each of the methods is described separately below, however it should be understood that whenever possible a device described for one method can be used for any of the other methods when practicable. Also, a key aspect of the invention is the measurement of electrical current through an electrolyte solution. For clarity, the invention is described in terms of mixed phases of electrically conductive aqueous solutions and electrically insulating oils. However it should be understood that the invention is not limited to aqueous solutions and insulating oils. The invention considers any two phase system exhibiting a difference in conductivity between the two phases. The invention considers broadly the interaction of spatially separated fluids and changes in their electrical characteristics. The physical phenomena, such as Laplace pressure, giving rise to certain capabilities of the methods are best exploited on the microscale, e.g. with microfluidic devices. Methods of fabricating microfluidic devices are well known to those of ordinary skill in the art and all microfluidic fabrication methods are considered by the invention. However, although the invention is described in the context of microfluidic chips, it is not limited in this regard. Any fluidic circuit capable of maintaining spatial separation and merging of fluids within a mixed phase is considered.

In one embodiment, the invention includes methods for characterizing droplets. In these methods, an electrical circuit is closed during the passage of a droplet through an interrogation zone creating a measureable burst of current dependent on the presence of the droplet. In the simplest embodiment, four microfluidic channels combine at an 'X' intersection, illustrated in FIG. 1. Two opposing channels, called the "side channels" herein or alternatively the "injection channels" or "injectors", contain continuous aqueous phases 6 and 7 with solubilized electrolytes that flow into the intersection. The fluid contained within a side channel is also called a "side fluid" herein. A third channel, called the "main channel" herein, contains a stream of droplets 1 that also flow into the intersection. A fourth channel, called the "exit channel" herein, carries the flow from the previous three channels out of the device.

The pressure of fluids 6 and 7 is poised such that a bolus of fluid 8 from each protrudes far enough into the intersection that close contact is made to the arriving droplets. In certain methods of the invention the pressure of fluids 6 and 7 is high enough to drive some fluid into the intersection, but not high enough to overcome the Laplace pressure that builds in opposition of flow as more fluid enters the intersection, decreasing the radius of the meniscus. In these methods, a steady state is achieved where the flow from the side channels eventually stops with boluses of fluid from each protruding some distance into the intersection. In other methods of the invention the pressure of fluids 6 and 7 is high enough to drive a substantial amount of fluid into the intersection such that the boluses eventually break off into discrete droplets after growing to a certain size. Although not limited in this regard, the frequency of this droplet generation is preferably lower than the arrival frequency of droplets 1 from the main channel. In this manner, the arrival of the droplets 1 from the main channel sets the pace of the fluid dynamics at the intersection.

Once a droplet 1 arrives from the main channel at the intersection, close contact between the droplet and the menisci of the continuous phases 6 and 7 allows the three spatially separated fluids to merge into one transient continuous phase 10. Shortly afterwards fluidic strain at the intersection snaps off the droplet 13 again, away from the side channels. The menisci 12 at the side channels reset before the arrival of the next droplet. Without wishing to be constrained by any theory, the ability of the spatially separated aqueous phases to merge spontaneously depends on the extent of surfactant stabilization at the surfaces. Unstable surfaces, such as in systems with no surfactant, little surfactant, or ineffective surfactants will merge spontaneously. Other systems are fully surfactant stabilized and require the application of a high electric field to rupture the surfaces. Both spontaneous and assisted merging are considered by the invention.

In one non-limiting example of spontaneous merging, the apparatus of the invention is placed directly downstream from a separate droplet generator. It is often desirable to provide a surfactant to prevent spontaneous coalescence of droplets collected from a droplet generator, but the surfactant loading at the surface of newly formed droplets requires some time to equilibrate, a process called droplet maturing. During the maturing stage, surfactant molecules repartition from the oil and/or aqueous phases into the interface, a dynamic diffusion-limited process that takes some time to reach a steady-state. In this example of the invention, the side channels are positioned sufficiently close to an upstream droplet generator that the newly formed droplets cannot mature before reaching the side channels. The immature droplets may spontaneously coalesce with the fluids in the side channels of the invention, even if the interfaces of the side fluids have already matured themselves. In certain surfactant systems, both contacting surfaces must be mature to prevent merging. In an alternative example, there is zero or insufficient surfactant present in the upstream aqueous and oil phases to prevent merging, and more surfactant is mixed in downstream at a later stage to stabilize the droplets in an emulsion.

In one non-limiting example of assisted merging, the apparatus of the invention is placed directly downstream from an emulsion reinjection nozzle. Often during storage of an emulsion the oil phase drains out of the emulsion leaving tightly packed droplets separated by surfactant and thin layers of oil. An emulsion reinjection nozzle, described for example by Zhong et al. (2011) in *Lab Chip*, 11, 2167-2174, is a common microfluidic device that separates packed droplets in a microfluidic channel by adding back a uniform amount of spacer oil between each droplet. The spacer oil often contains surfactant itself to continue emulsion stabilization after any microfluidic manipulations. Hence in this common example all of the interfaces, both for droplets and side fluids, are mature. In these cases a high electric field is necessary for merging and it can be provided by any means. The invention is not limited in this regard, however the most common method is to incorporate pairs of electrodes proximate to the fluidic channels within the microfluidic device and then apply a high oscillating voltage across them. In the preferred embodiment, the electrodes are placed in direct electrical contact with the side fluids, as described below.

As illustrated schematically in FIG. 1, in certain embodiments of the invention, a pair of electrodes 2 and 3 is placed in direct electrical contact with the side fluids for several possible purposes including, but not limited to measuring electrical continuity and initiating fluidic merging. The electrodes may be of any type and many types are known to those of ordinary skill in the art, including but not limited to metals like gold and platinum; semiconductors; organic conductors; and redox couples such as Ag|AgCl. A voltage 4 is applied between the electrodes, either DC or time-varying, driving an electric current dependent on the electrical resistance of the circuit. Many methods of creating an electrical voltage are known to those of ordinary skill in the art, and all are considered by the invention. The current flowing through the electrodes is measured with an ammeter 5. Many methods of measuring electric current are known to those of ordinary skill in the art, and the invention is not limited in this regard. All methods of measuring current are considered. Although the voltage source, the electrodes, and the ammeter are illustrated in a particular order in FIG. 1, it should be understood that many different electrical circuit configurations serving the same purpose will be apparent to those of ordinary skill in the art, and the invention is not limited in this regard.

The electrical resistance varies in time in certain methods of the invention, dependent on the presence of a transient electrolyte bridge formed by droplets within the fluidic intersection of the microfluidic device. These droplet-dependent variations in resistance are measured directly as bursts of electric current, as illustrated in FIG. 1. Before the arrival of a droplet 1 an insulating oil gap separates the conductive side fluids, establishing a high electrical resistance and therefore a low current reading 9. On merging of the droplet 10 with the two side fluids the resistance drops, indicated by a high current reading 11. After departure of the droplet 13 from the intersection, the oil gap reappears returning the current to the original low reading 14. In this manner, bursts of electric current indicate the passage of individual droplets through the intersection. Methods of the invention comprise counting droplets from current bursts; measuring droplet frequencies from the droplet count as a function of time; measuring initial droplet volumes as the flow rate of the aqueous phase (giving rise to the stream of droplets) divided by the frequency; and directly measuring droplet size as indicated by the width of the current pulse.

Figure 5:
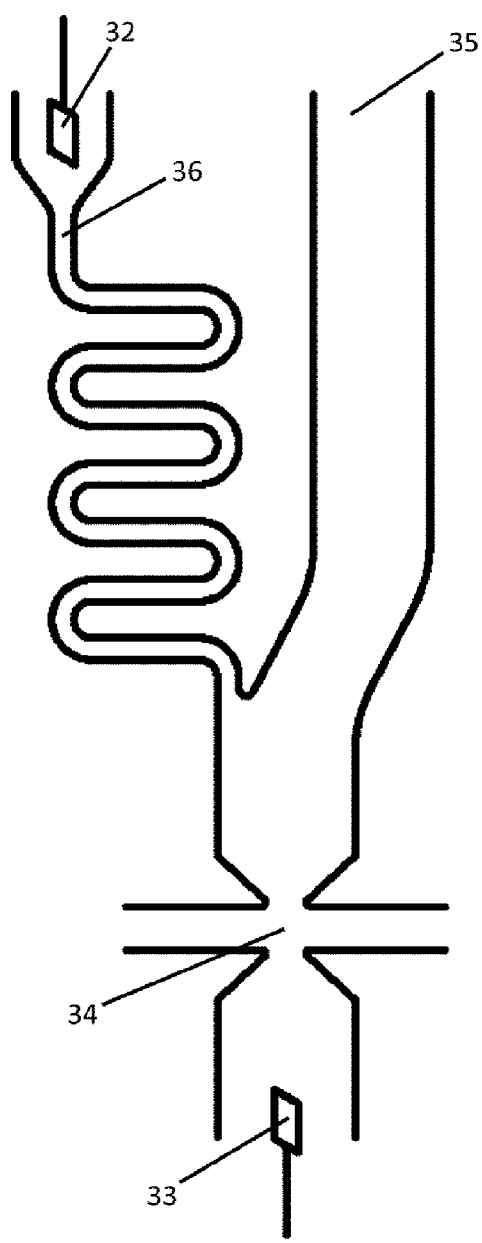
FIG. 5 shows a bifurcated side channel.

In those methods of the invention using electrodes in direct contact with the side fluids, electrons must transfer between the solution and the electrodes and charge carriers must be present within the solution to complete the electrical circuit according to electrochemical guidelines known to those of ordinary skill in the art. Each electrode constitutes an electrochemical "half-cell" where at one electrode, the cathode, a species is chemically reduced (electron injected) and at the other electrode, the anode, a species is chemically oxidized (electron abstracted). Redox couples such as the common Ag|AgCl electrode can be used at low voltages of ~1 V or less, however depending on the fluidic circuit and the ionic strength of the electrolytes the current produced at low voltages may be challenging to measure. At voltages higher than 1.23 V, the standard potential of water electrolysis, water splitting into hydrogen and oxygen gases occurs at the cathode and the anode respectively. While convenient as an inherent pair of redox couples present in any aqueous system, gas production at the electrodes can pose challenges for closed fluidic systems such as piston driven pumping systems. Gas accumulation increases the pressure and the fluidic compliance, potentially altering the intended flows and causing sluggish behavior in controlling flow within the microfluidic system. Thus fluidic systems driven by fixed pressure conditions, as opposed to fixed flow rate, may be preferred for high voltage electrodes that produce a significant amount of gas. Otherwise the current can be limited, even in the case of high voltage electrodes, either by incorporating high electrical resistance into the microfluidic channels or with low conductivity buffers. However, the buffer composition is often restricted by the application, and the fluidic resistance is affected by the same changes in the microchannels that impact the electrical resistance. To overcome any undesirable tradeoffs in electrochemical vs. microfluidic design, parallel channels can be employed separating the high electrical resistance necessary for an electrochemical circuit from the low fluidic resistance that may be necessary for the fluidic circuit. In one example of the invention, illustrated in FIG. 5, a pair of fluidic ports on a microfluidic chip are fluidically connected to a pair of channels 35 and 36 that intersect into a single channel that becomes a side channel in the invented device. The two parallel channels are different, one is either longer or narrower or both, providing a higher fluidic and electrical resistance. An electrode 32 is positioned in the port of the high resistance channel 36 providing a high resistance electrical circuit. Pressure is applied to the port of the low resistance channel 35 yielding a flow into the side channel of the invention, and also into the high resistance channel. If any flow into the high resistance channel is undesirable, then the same pressure can be applied to both ports simultaneously eliminating the issue. Thus methods of the invention provide a variety of means to combine hydrodynamic flows with electrochemical currents in the same device, at either low or high voltages. While this example specifically addresses a possible need for two different fluidic paths for hydrodynamic flow and electrical current in certain circumstances, and while in other cases the same path can be used for both, it is understood that there many different ways apparent to those of ordinary skill in the art to establish electrical and hydrodynamic connections within fluidic circuits. All such methods are considered by the invention.

One advantage of delivering the electrical field via solution in the side channels is that surfactant-stabilized interfaces will rupture at much lower applied voltages than typically required with proximate electrodes patterned into the chip. Similar to a parallel plate capacitor, when a voltage is applied across the pair of electrodes contacting the two side fluids of the invention that are separated by an oil gap, electrolytes flow through solution until charge accumulation at the water-oil interface produces an electrical field that opposes the applied voltage. Due to the very short distances between the interfaces, typically tens of microns in the absence of droplets in the intersection and much shorter with droplets present, extremely high strength electrical fields are created from modest voltages. In contrast, due to manufacturing limitations patterned electrodes are often spaced 20-50 µm away from fluidic channels reducing the electrical field in proportion to the distance. Furthermore, geometrical constraints with patterned electrodes often lead to field orientations that are not optimal for merging. Consequently voltages of 500 V and higher are often used for merging droplets with patterned electrodes. However, 500 V applied directly across an oil gap of 20 µm for example, as might be the case for the electrified side channels in certain embodiments of the invention, results in an electrical field of 25 MV/m exceeding the dielectric breakdown voltage of common oils such as silicon and mineral oil. Furthermore, when a droplet enters the intersection the oil gaps can drop below 1 µm resulting in field strengths exceeding 500 MV/m, higher even than the dielectric breakdown of exquisite insulators like mica and Teflon. The geometrical advantage of delivering the electrical field via solution translates into lower required voltages in the range of 0.1-10 V, easily accomplished with low cost semiconductor devices and much preferred over the expensive and dangerous high voltage amplifiers and transformers otherwise typically used for driving patterned electrodes.

Figure 2:
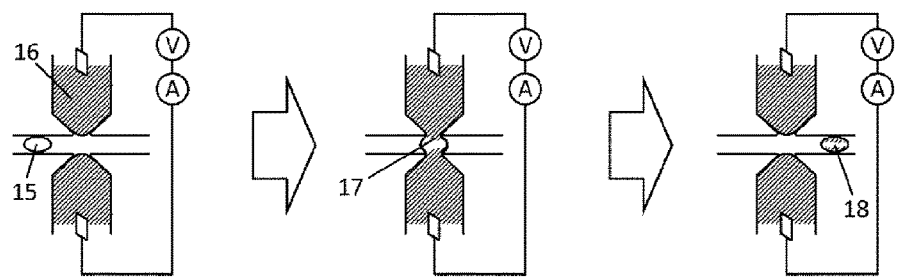
FIG. 2 shows adding reagents to a droplet.

In certain embodiments of the invention the contents of the side channels mix with the droplet contents during the excursion of the droplet through the fluidic intersection. Illustrated in FIG. 2, in certain methods of the invention the side channels inject fluid 17 into the arriving droplets 15 that remains captured within the droplets 18 after snap-off and later mixes within the droplet. The side fluids may contain reagents, beads, cells, or any other chemical, biochemical, or material that can be solubilized or suspended in aqueous solution. Thus, this method of the invention is a droplet injector. For proper operation, the pressure of the side fluids 16 must be higher than the internal pressure of the arriving droplets 15. The internal pressure of the arriving droplets 15 is driven by the confinement into a microfluidic channel, whereas the pressure of the side fluids is set externally by the pressure source driving flow. If the radius of curvature of the menisci of the side fluids is smaller than the radius of curvature of the arriving droplets, the Laplace pressure of the side fluids will be higher, setting up the right condition for flow from the side channels into the droplet on merging. In certain methods of the invention the same fluid is injected from both side channels, and in other methods of the invention different fluids can be injected. The latter case is especially important when the added fluids contain species that are chemically reactive with each other and require separation until the moment of mixing within the droplets.

Figure 4:
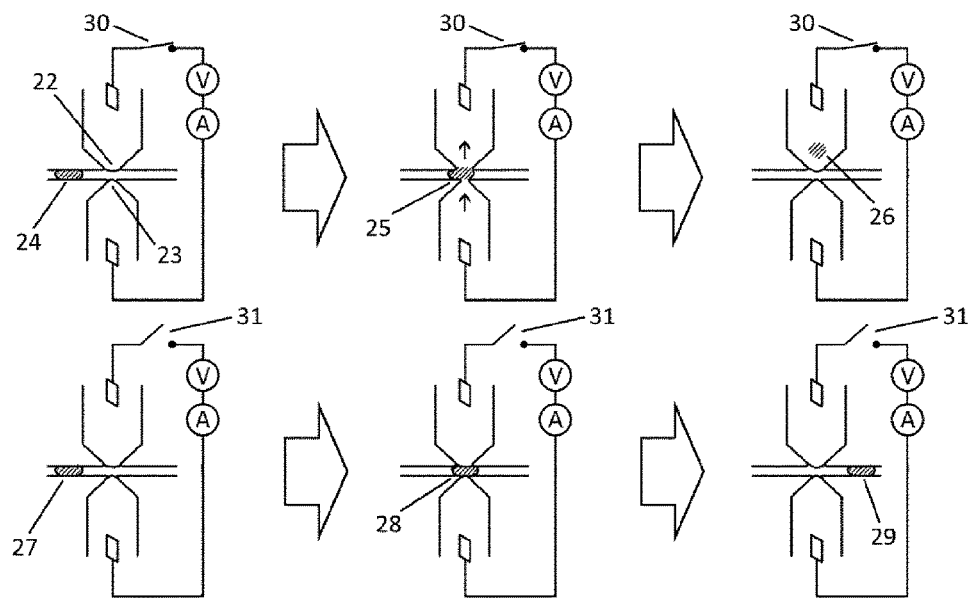
FIG. 4 shows selective droplet sorting.

In other embodiments of the invention the side channels extract fluid from the droplets, illustrated in FIG. 4A-C. In these methods of the invention, arriving droplets 24 are constrained such that their internal pressure exceeds the pressure of the side fluid 22 causing the droplet contents to flow into the side channel on merging. The methods of the invention are not limited to symmetrical intersections and equal pressures at the side channels; rather the invention is unlimited in this regard. The pressures of the side channels can be similar or different, and the orifices of the side channels entering the intersection can be similar or different as well. As illustrated in FIG. 4A-C, the system can be poised as both an extractor and an injector simultaneously. In this method of the invention, the pressure of the injector channel 23 is higher than the internal pressure of the arriving droplet 24, and the pressure of the extractor channel 22 is lower than both. Hence, on merging either some or all of the contents of the droplet flow into the extractor channel along with some fluid from the injector channel. After the droplet is either consumed or snaps off again, the extracted contents of the droplet 26 remain captured in the extractor channel.

In certain embodiments of the invention droplet injection or extraction is selective. In one non-limiting example, illustrated in FIG. 4, droplet extraction may be triggered by an upstream fluorescence measurement similar to fluorescence assisted cell sorting (FACS). In this example of the invention, droplets 24 with a particular fluorescence signature, such as those containing a high fluorescence signature, are identified upstream by fluorescence measurement that triggers on the voltage source for merging 30. After excursion into the intersection the contents of these droplets 26 are extracted in the side channel 22. Other droplets with low fluorescence 27 do not trigger the voltage source 31 and hence they bypass the extractor 29.

In contrast to the previous embodiments, for certain applications minimal mixing of the droplet contents with the side channels may be desired. Methods of the invention also facilitate minimal mixing. Without wishing to be constrained by any theory, the least mixing is typically achieved when the internal droplet pressure equals the pressure within the side channels, however the perfect balance may be difficult to obtain. The impact of pressure imbalances on mixing can be attenuated by increasing the fluidic resistance of the side channels. In this method of the invention high resistance features within the channels will limit any injection or extraction flow that would otherwise arise from pressure imbalances. For microfluidic implementations with high compliance, such as elastomeric chips, the resistors should be placed close to the intersection to avoid transient flows that bypass the resistors. Otherwise the invention is not limited with regard to size, shape, or placement of the resistive fluidic elements.

Figure 3:
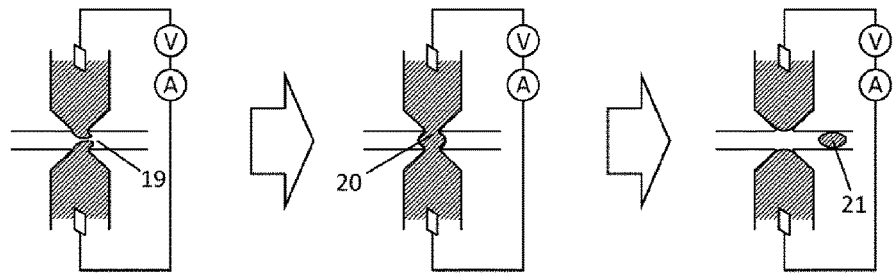
FIG. 3 shows generating a droplet.

In yet other embodiments of the invention the side channels act together as a droplet generator. Illustrated in FIG. 3, no droplets enter the device in the main channel as described for other methods of the invention. Rather, the pressure of the side channels is poised such that boluses of fluid protrude far enough into the intersection that they contact each other 19 and merge 20. Merging may be spontaneous or assisted by an electrical field. Once merged, the aqueous phase spans the gap between the electrodes allowing electronic continuity measurements of droplet formation, as described above. The merged droplet continues growing until fluidic strain from the oil flowing in the main channel snaps off the new droplet 21. This process continues repeating, generating a stream of uniformly sized droplets while allowing simultaneous electrical monitoring of droplet generation. The carrier oil in the main channel may contain surfactant to stabilize the droplets in an emulsion downstream. The surfactant may stabilize the interface of the growing boluses even as they emerge into the intersection, in which case a high electrical field may be required to rupture the interface. However, in other cases the surfactant may not be present, or may be of insufficient quantity or capability, or may not mature quickly enough to prevent spontaneous merging. Regardless, although unnecessary in these cases to assist merging, the electrical system may still be employed for monitoring droplet generation. Extra surfactant may be mixed into the oil stream afterwards to stabilize the droplets in an emulsion.

The invention has been described thus far in terms of a single pair of side channels, optionally matched with a pair of electrodes either proximate to the fluidic channels or in direct fluidic contact with the side fluids, and at right angle geometries with respect to the main and exit channels. However the invention is not limited in regard to the number of intersecting channels, nor the number or placement of the electrodes, nor the angles at which channels intersect, nor the relative sizes of the channels, nor the types of electrodes. The invention considers any number of channels that can achieve transient fluidic continuity in a mixed phase fluidic system that are combined in a network in any geometrical arrangement and without restriction to the relative sizes or to symmetrical or asymmetrical designs. The invention also considers any arrangement of any types of electrodes, including no electrodes, that may be necessary for assisting in fluidic merging and optionally for monitoring electrical continuity within the network.

The invention has also been described thus far in terms of a single fluidic circuit, however complicated. It will be clearly evident to those of ordinary skill in the art that aspects of the invention can be combined and repeated within a single device. It should be understood that the invention considers any plurality and combination of the methods and apparatus described herein.

The invention has also been described thus far in terms of similar aqueous fluids contained in the side channels and within droplets, however the invention is not limited in this regard. Those of ordinary skill in the art will envision many combinations of different fluids, aqueous or otherwise, that can be implemented according to methods of the invention. Any such combination of fluids is considered by the invention.

The invention has also been described thus far in terms of resistance measurements for simplicity, however the invention is not limited in this regard. Those of ordinary skill in the art will appreciate that electrical resistance is just one component of complex electrical impedance that also includes capacitance and inductance. The complex impedance is the generalized opposition to current that a circuit imposes when a time-varying or constant voltage is applied. The invention considers any impedance measurement that indicates the passage of a droplet between two or more continuous phases of the same or different types. In particular, the invention also considers the case that the droplets do not merge with the side fluids in which case capacitance becomes a critical aspect of impedance characterization. The thin layers of surfactant and oil that separate the conductive fluids introduce electrical capacitance in series with the electrical resistance of the fluids. Similar to a parallel plate capacitor, the capacitance increases with decreasing distance between interfaces. Arrival of droplets within the intersection reduces the oil gap dramatically, and hence a burst of increased capacitance accompanies droplet occupancy that is used by methods of the invention to indicate the presence of a droplet. Those of ordinary skill in the art will recognize that there are many ways to analyze electrical signals that indicate impedance changes, and all such methods are considered by the invention. Those of ordinary skill in the art will also recognize that numerous current driving schemes exist, such as lock-in amplification, filtration, etc. that enhance electrical signals, such as improving signal-to-noise ratios. All such signal enhancement schemes are also considered by the invention.

The invention has also been described thus far in terms of simplistic event-based interpretation of impedance changes to characterize droplets. For example, discrete droplet counting based on resistance changes has been described as a means to measure droplet frequency by monitoring droplet counts as a function of time. Those of ordinary skill in the art will readily appreciate that many analysis approaches exist to derive count, frequency, and volume measurements from data provided by methods of the invention, and the invention is not limited to the analysis examples provided herein. As one non-limiting example of alternative analysis techniques, Fourier analysis is commonly used for frequency analysis, and is also considered by the invention. Nor is the invention limited to the types of results from data analysis described above, namely droplet count, frequency, and volume. Rather, those of ordinary skill in the art will readily envision other analytical results that can be obtained for impedance changes as a function of time, with non-limiting examples including statistical analysis of droplet sizes, droplet velocities, flow rates, etc. The invention considers all such analytical results.

The invention also encompasses methods for highly sensitive and specific detection of DNA molecules using the microfluidic methods of the invention as the preferred embodiment, but not limited to the microfluidic methods of the invention. These biochemical methods will be described in the context of the detection and discrimination of genetic variants, but the invention is not limited in this regard. DNA detection and characterization are considered for all types of DNA molecules and for all applications. The invention also envisions DNA detection and characterization for indirect quantitation of other macromolecules, for example for RNA detection when accompanied by reverse transcription of RNA into DNA or for any other signature of a macromolecule that can be indicated by or transformed into the presence of DNA. The invention also envisions capture and quantitation of any biological molecule with either native or augmented ability to participate in free radical polymerization and thus become entrapped in microgels.

In all aspects of the invention, DNA is provided for quantitation with sufficient purity necessary for performing PCR amplification and without impurities that could disrupt sample emulsification. Numerous DNA purification methods are known to those of ordinary skill in the art, such as chemical extraction with chloroform/phenol, size exclusion by ultrafiltration, binding to microporous matrices, salting-out, cesium chloride density gradients, and adsorption to silica-gels, but the invention is not limited in this regard. Any purification method capable of supporting PCR and emulsification is considered, however in practice purification by user friendly "kits" such as the Qiagen QIAquick is most often adequate. In certain applications yielding very long DNA strands, typically longer than 3 kb, the purified DNA may need to be fragmented into smaller pieces to reduce the solution viscosity to levels suitable for emulsification, also depending on the method of emulsification. For example, human genomic DNA from cell culture typically requires mechanical shearing prior to injection into microfluidic emulsifiers because it is isolated in very long strands. In contrast, circulating free DNA (cfDNA) from the bloodstream of humans that arises from dying cells is generally broken down into much smaller fragments and does not require further fragmentation (see Jahr et al., *Cancer Res.*, 61, 1659-1665, 2001). Acceptable methods for DNA fragmentation include mechanical shearing, nebulization, sonication, vortexing, acoustical conditioning (a.k.a. Covaris), and restriction enzyme digestion, but the invention is not limited in this regard. Any fragmentation method known to those of ordinary skill in the art will suffice, however nebulization is simple and most often adequate. Restriction enzyme digestion is advantageous for applications that suffer bias from random fragmentation. One example is copy number variation that compares the quantity of one DNA target to another. If the amplicon length for one target is much longer than the other its concentration will be underestimated with random fragmentation due to the increased chance of strand breakage between the primer binding sites. While this error is systematic and can be controlled, it leads to non-integer copy number measurements requiring further explanation. Restriction enzyme digestion can be a better approach in these cases, avoiding altogether any fragmentation within target regions. Certain emulsification techniques may also be more susceptible to long DNA fragments. Microfluidic droplet generators generally do require some degree of fragmentation, whereas emulsification by vortexing for example inherently fragments the DNA during droplet generation itself and thus may tolerate longer molecules. Ultimately the proper DNA fragmentation and emulsification methods are interdependent, and the invention contemplates any such pairing of methods that are mutually compatible.

Figure 6:
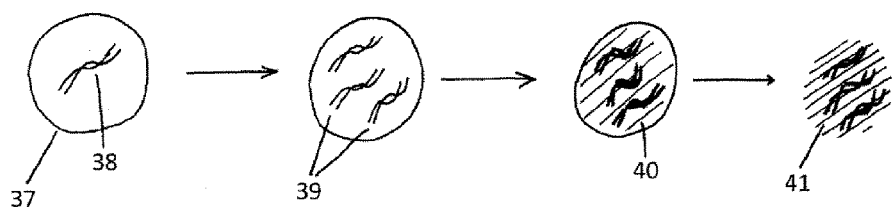
FIG. 6 shows the product of single DNA molecule amplification incorporated into a gel matrix.

Illustrated in FIG. 6, after purification the DNA sample is emulsified at limiting dilution such that each droplet 37 likely contains only one or zero DNA molecules 38 targeted by the multiplexed assay. The water-in-oil emulsion is created by any method known to those of ordinary skill in the art including, but not limited to, mixed phase agitation by vortexing, mechanical mixing (e.g. magnetic stirring), sonication, bead beating, and filtration. These approaches yield somewhat non-uniform distributions of aqueous droplet sizes. Alternative microfluidic methods for emulsion generation are also suitable, including, but not limited to, droplet generation in shearing (see Thorsen et al., *Phys. Rev. Lett.*, 86(18), 4163-4166, 2001), elongational (see Anna et al., *Appl. Phys. Lett.*, 82(3), 364-366, 2003), or mixed fluidic strain flows. The microfluidic methods generally yield highly uniform distributions of droplet size, an advantage for applications requiring high sensitivity and uniform reaction yields on a per target molecule basis. High droplet size uniformity is also desirable for certain downstream processes in the invention, such as for some microfluidic methods for adding prepolymer to existing droplets on a one-by-one basis, however the invention is not limited in regards to the extent of droplet size uniformity. The minimum quality of the emulsion will be dictated by the application and the downstream processing.

The aqueous phase in the emulsion comprises the template DNA, PCR primers, a DNA polymerase, nucleotide triphosphates (a.k.a. dNTPs), salts and buffers as required to sustain in vitro DNA amplification. This mixture is referred to as the "PCR mixture" for simplicity throughout the descriptions here. In the preferred embodiment the polymerase is thermostable, enabling PCR by thermal cycling, however the invention is not limited in this regard. Instead of standard PCR primers, the aqueous phase may contain alternative primers for different PCR strategies and for post-processing of the amplicons. Many different PCR strategies are known to those of ordinary skill in the art, and all are considered by the invention. Some of the most common PCR strategies include allele specific PCR, CAST-PCR, PCR with MyT primers, asymmetrical PCR, COLD-PCR, Ice-COLD-PCR, and touch-down PCR. Isothermal amplification methods such as helicase-dependent amplification, rolling circle amplification, recombinase polymerase amplification, and strand-displacement amplification are also considered by the invention. Any method of DNA amplification that maintains the isolated environment for individual DNA molecules is considered by the invention.

The aqueous phase may also contain probes for detecting the presence of DNA after amplification and capture within a hydrogel. DNA probes are either sequence-specific or non-specific. Sequence-specific probes include TaqMan, scorpion, strand displacement, PNA, LNA, molecular beacon, Solaris, fluorescently labeled DNA oligomers, and DNA binding proteins. Non-specific probes include ethidium bromide, SYBR-green, bis-intercalators (e.g. YoYo-1), and DNA binding proteins. The invention is not limited to these specific- and non-specific probes. Many DNA probes are known to those of ordinary skill in the art, and all are considered by the invention. However the preferred embodiment of the invention does not employ probes before amplification and gelification. Rather, as described in detail further below, there are advantages to waiting for gelification and particle washing before hybridization with sequence-specific probes. Generally fluorescent probes are preferred due to their high sensitivity, abundance in many colors and attachment chemistries, and straightforward detection with high throughput. However at the high concentrations of amplified DNA arising from methods of the invention, primers with modifications supporting alternative methods of DNA detection are considered including but not limited to electrochemical methods, absorbance, and radioactive labeling.

The aqueous phase may also contain some or all components of the prepolymer mixture for droplet gelification. The prepolymer mixture comprises the monomers (the individual molecules bound together during polymerization), one or more initiators of polymerization, and optionally porogens present to increase the porosity of the hydrogels. For an example of one method for tuning the porosity of hydrogels considered by the invention, see Choi et al., *Anal. Chem.*, 84, 9370-9378, 2012, however the invention is not limited in this regard. Any method of tuning the pore size of hydrogels known to those of ordinary skill in the art is considered by the invention.

The invention allows DNA amplification and gel polymerization to occur in either order, or simultaneously, imposing different constraints on the prepolymer mixture. In one embodiment, all of the prepolymer components are added to the PCR mixture prior to emulsification and thermal cycling. In this embodiment all components of the prepolymer mixture must be thermally stable at the temperatures required for PCR unless gel polymerization precedes DNA amplification. Alternatively the aqueous phase may contain none of the constituents of the prepolymer. In this case the prepolymer must be added to the droplets after thermal cycling by selectively merging aqueous phases or via the oil phase as described in detail further below. Lastly the aqueous phase may contain some of the prepolymer, either containing a lower overall prepolymer concentration or with fewer constituents or both. In any scenario that the prepolymer is incomplete after emulsification, the remainder must be added without disrupting the emulsion using methods described further below.

The oil phase comprises two primary components: one or more hydrophobic oils and zero, one, or more surfactants for emulsion stabilization. The invention considers all oil phase compositions that stabilize an emulsion throughout DNA amplification, and without wishing to be bound by any theory, it is generally understood that surfactants assist in preventing droplet coalescence. Suitable oils include hydrocarbon oils such as mineral oil, TegoSoft DEC, tetradecane, hexadecane, octadecane, dodecane, Isopar M, vegetable, and organic; silicon oils such as DC200, PDMS, and AR20; and fluorinated oils such as PFH, PFC, PFD, PFPH, HFE, Novec, FC40, FC70, FC77, and FC3283. Suitable hydrocarbon surfactants include SDS, Span80, monolein oleic acid, Triton X-100, Tween 20, Tween 80, Synperonic PDF, C12E8, phospholipids, and Abil WE09. Suitable fluorocarbon surfactants include PF-octanol, PF-decanol, PF-TD OEG, PFPE-COOH, PFPE-COONH$_4$, PFPE-PEG, and PFPE-DMP. However the invention is not limited in this regard. Any surfactant system capable of stabilizing an emulsion throughout DNA amplification is considered by the invention.

The oil phase may also contain reaction constituents that can re-partition into the aqueous phase after mixing the two phases. Without wishing to be bound by any particular biochemical system, the PCR mix generally comprises hydrophilic components that partition poorly into the oil phase. However small molecules like salts can be dissolved via surfactant micelles into the oil, depleting the amplification reaction of necessary enzyme cofactors or reactants. Pre-saturation or pre-loading of the oil phase with these transportable compounds can mitigate reactant re-partitioning and rescue performance. Additionally some constituents of the prepolymer mix may partition partially or preferably into the oil direction, or be solubilized by the surfactant. Either to rescue the gel polymerization or to intentionally isolate some component of the prepolymer mixture, prepolymer components can be added to the two-phase system via the oil phase in addition to or instead of the aqueous phase. Methods of the invention anticipate this alternative formulation of the two-phase system, and the methods are not restricted in this regard. Any two-phase formulation that allows for amplification of DNA within droplets followed by gelification is considered, and any two-phase formulation that allows for gelification followed by amplification of DNA is considered.

Optionally, in the case that the PCR mix and prepolymer mix are combined before emulsification, the prepolymer may be partially cured after emulsification to discourage droplet coalescence during amplification. Thermal cycling stresses the emulsion, potentially providing sufficient activation energy for forming pores between the molecular monolayers of surfactant that otherwise obstruct direct contact of the aqueous phases of neighboring droplets. Once the aqueous phases make contact through an initial pore, surface tension drives coalescence irreversibly. Partial gelification may allow flickering pores to heal before coalescence or substantial mixing of neighboring droplets. The effectiveness of partial gelification depends on the extent of polymerization, a process variable that can be optimized to minimize coalescence while maintaining rapid and uniform DNA amplification throughout the droplets.

Illustrated in FIG. 6, after emulsification either the target DNA is amplified 39 or gel polymerization is initiated 40, or both. The description focuses first on the case that the target DNA is amplified first. Numerous DNA amplification strategies are known to those of ordinary skill in the art, including but not limited to amplification by thermal cycling of a thermostable DNA polymerase and isothermal DNA amplification. Thermal cycling of stationary samples is typically accomplished with a temperature controlled heating block in close thermal contact with the samples. Alternatively the sample can be displaced between different temperature zones, most conveniently by flowing the sample through zones of different temperatures. However any method of heating and cooling a sample is considered by the invention for DNA amplification by thermal cycling, as is any method of isothermal DNA amplification. Droplets that have undergone DNA amplification are referred to as "amplified droplets" for simplicity from this point forward.

Depending on the droplet formulation, additional prepolymer reagents may need to be added to the aqueous and/or oil phases after DNA amplification. In one embodiment the sample solution contains the complete PCR and prepolymer mixes prior to emulsification, in which case polymerization can be initiated or continued after DNA amplification. However, in embodiments of the invention lacking some components of the prepolymer mix, these components must be added to the aqueous phase after DNA amplification. The primary reasons to separate reactants in this manner are, first, if the prepolymer reactants are not stable at the high temperatures of thermal cycling, and second, if the prepolymer reactants hinder DNA amplification. In the case that the prepolymer mixture is incomplete after DNA amplification, the missing components of the prepolymer must be added to the aqueous phase without disrupting the emulsion and causing significant droplet coalescence such that the clonal amplicons become mixed. Without wishing to be bound by any theory, droplet coalescence generally reduces the information content in the results since the contents of coalesced droplets may not be clones from a single copy of DNA.

In one set of methods considered by the invention for adding prepolymer reagents to amplified droplets, controllable amounts of prepolymer reagents are added to each droplet by merging two or more aqueous phases together. Any technique for adding reagents to droplets is considered by the invention, including but not limited to the following: paired droplet merging (see U.S. patent application Ser. No. 12/729,462, filed Mar. 23, 2010, entitled "Manipulation of Microfluidic Droplets", by Miller et al., published as U.S. Patent Publication No. 2011/0000560 on Jan. 6, 2011), picoinjection (see description above), lambda-injection (see description above), and others known to those of ordinary skill in the art. While the invention considers any combination of prepolymer constituents in any arrangement with regard to the internal plumbing of the merge device, it is generally good practice to physically isolate the gel monomers from the initiator until the merge occurs to prevent device clogging by premature polymerization. Furthermore certain DNA amplification methods may be inhibited by gel monomers or initiators, possibly imposing other constraints for separation. The microfluidic methods of the invention are therefore preferred for simplicity and flexibility over the other methods because only the methods of the invention allow all three aqueous samples—amplified droplets, monomers, and initiator—to be isolated until a single merge event occurs. The other common microfluidic methods all involve injection from a single aqueous stream into droplets, hence requiring either some premixing or else merge operations in multiple stages.

In another set of solutions for adding prepolymer constituents to the amplified droplets, the missing prepolymer reagents are added to the droplets through the oil phase by re-partitioning. Without wishing to be bound by any particular biochemical arrangement, the polymerization initiator is generally best suited for injection into the amplified droplets through the oil because the other gel components are typically insoluble in oil, but the invention is not limited in the regard. In this method of the invention, the chemical composition of the oil is changed such that the initiator, or any other component of the prepolymer mixture, present in the oil partitions into the aqueous phase. In the simplest embodiment, the amplified droplets are exposed to a different oil containing the missing prepolymer constituents either by mixing in the new oil or replacing the original oil. In this embodiment, some fraction of the oil solutes will displace into the aqueous phase according to the partition coefficients. However these prepolymer constituents arriving from the oil phase are consumed during polymerization in the aqueous phase, hence mass action drives a continuous flux of these compounds into the amplified droplets even if the partition coefficients are low. The invention considers any method for disrupting the equilibrium balance of prepolymer constituents in the oil phase and aqueous phases. Alternative methods include but are not limited to initiating a chemical reaction that frees one or more prepolymer constituents into solution within the oil and initiating a photochemical reaction that frees one or more prepolymer constituents into solution within the oil.

In the case that the original oil is mixed with a new oil that contains one or more missing prepolymer constituents, the two oils do not need to be miscible. One arrangement considered by the invention is to perform DNA amplification using a fluorinated oil, and then to mix in a hydrocarbon oil afterwards that contains the missing prepolymer constituents. The high density fluorinated oil will spontaneously drain from the droplets, exposing them spontaneously to the hydrocarbon oil. However the invention is not limited in this regard. Any combination of oils, miscible or otherwise, is considered by the invention.

After any remaining prepolymer constituents are added, if even necessary, to the amplified droplets, gel polymerization either continues or is initiated. There is no restriction in the invention whether gel polymerization starts before DNA amplification and continues throughout; or gel polymerization is initiated before DNA amplification to provide an initial gel scaffold, followed by completed polymerization after DNA amplification; or gel polymerization is completed before DNA amplification; or all of the gel polymerization occurs after DNA amplification. In the preferred embodiment, DNA amplification and gel polymerization are isolated events in time. Without wishing to be constrained by any biochemical arrangement, there are generally two methods to isolate the two processes: withhold one or more key reactants for gel polymerization until after DNA amplification, or activate the gel polymerization reaction afterwards. In the latter case, UV light activation of photoinitiators is the most common technique, although the invention is not limited in this regard. Any method of gel polymerization that does not interfere with DNA amplification is considered by the invention.

In the case that some or all of the prepolymer constituents are added to the droplets via the oil phase, the polymerization within the particle may not be uniform. At one extreme condition, the particle periphery may be polymerized into a rigid and permselective shell, confining the amplicons inside by size exclusion but allowing smaller reagents such as hybridization probes to diffuse into the fluid interior. In another condition the gel matrix is completely uniform throughout the particle. In yet another extreme condition, the oil phase contains an inhibitor of polymerization, most commonly molecular oxygen, resulting in a dense gel at the center of the particles. The invention considers all conditions within these extremes.

In one embodiment, the initiator is Darocur™, a photoinitiator, and the gel monomer is polyethylene glycol diacrylate (PEG-DA). Other UV initiators are known to those of ordinary skill in the art, such as Irgacure™. Many gel monomers are also known to those of ordinary skill in the art, including acrylamide and bis-acrylamide. However the invention is not limited in this regard. Any combination of photoinitiators and gel monomers is considered by the invention. After the DNA amplification, and after addition of any remaining prepolymer constituents if necessary as described above, the amplified droplets are rigidified by UV light activation in bulk.

In the preferred alternative embodiment, the initiator is a common combination of tetramethylethylenediamine (TEMED) and ammonium persulfate, a chemical initiator, and the gel monomer is a mixture of 19:1 acrylamide/bis-acrylamide. Acrylamide is preferred over PEG-DA, despite the neurotoxicity of acrylamide, because PEG can destabilize certain emulsions. Many chemical initiators are known to those of ordinary skill in the art, however the invention is not limited in this regard. Any combination of chemical initiators and gel monomers is considered by the invention. The invention is not limited with regard to the method of adding the prepolymer constituents. Any fluidic arrangement that maintains the integrity of the emulsion and does not cause premature gel polymerization is considered by the invention. One advantage of chemical initiation instead of UV initiation is that UV light may damage the DNA amplicons, potentially hindering downstream DNA characterization. However, while commonly handled in biochemistry laboratories, the use of TEMED does require extra safety precautions.

In one embodiment of the invention, the DNA amplicons are bound within the gel matrix. The invention is not limited with regard to the specific chemistry of amplicon attachment to the gel matrix. Rather any chemical, biochemical, or physical attachment strategy is considered by the invention. In the preferred method of the invention, the primers used for DNA amplification contain a 5'-modification with Acrydite™. After DNA extension during PCR the resulting strand retains the 5'-Acrydite™, and when hybridized to a complementary strand synthesized from another Acrydite™ primer, the resulting amplicons contain two Acrydite™ moieties with one on either end. Acrydite™ reacts with activated double bonds during conventional free radical polymerization, incorporating the attached amplicons into the growing polymer chain (see Kenney et al., BioTechniques, 25, 516-521, 1998). Acrydite™ is the preferred chemistry for direct incorporation via primers because it is known to withstand the high temperatures of thermal cycling, however the invention is not limited in this regard. Any chemical attachment strategy is considered by the invention, as well as any configuration regarding whether one end of the amplicon, the other, or both ends are functionalized for incorporation into the gel matrix.

Figure 9:
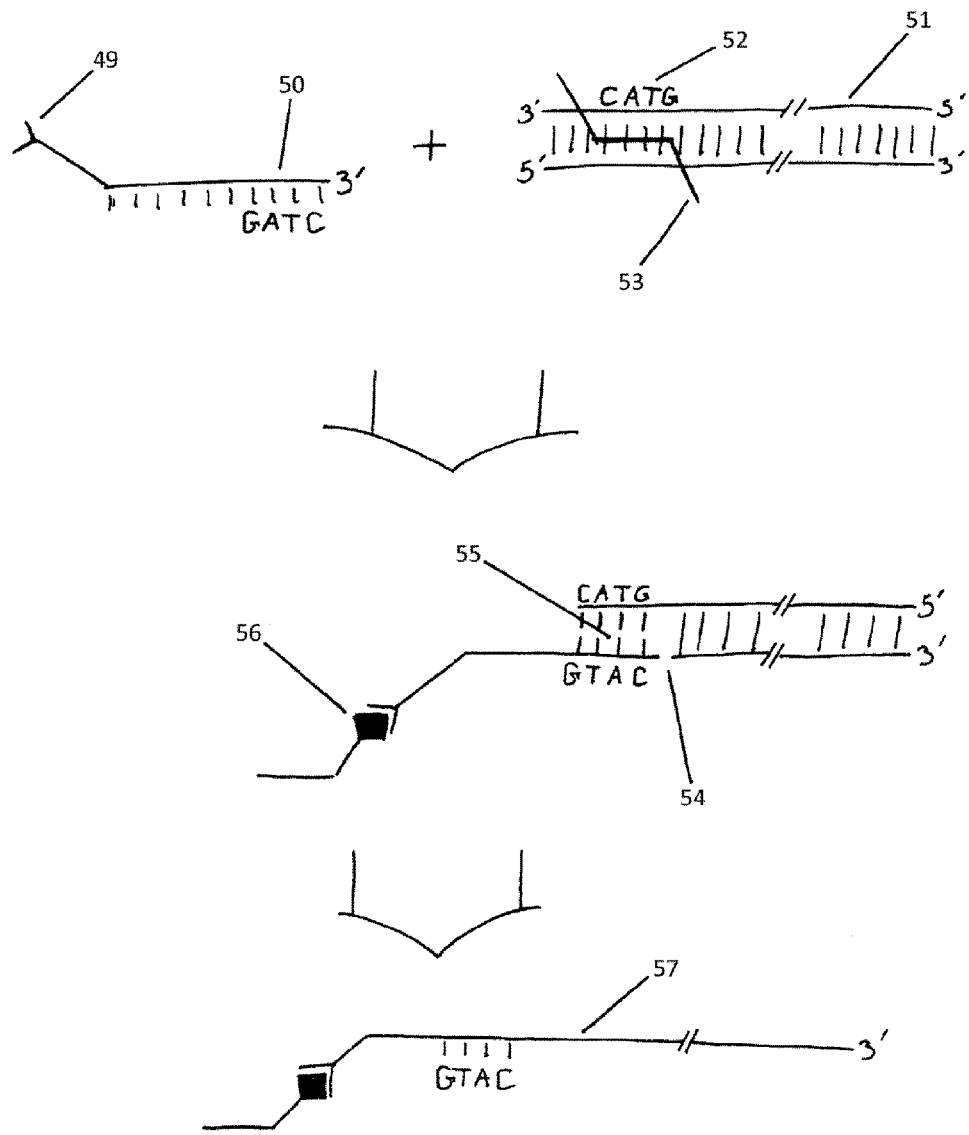
FIG. 9 shows covalent incorporation of single stranded DNA into a hydrogel matrix.

Alternatively, illustrated in FIG. 9, less stable attachment chemistries can be introduced after thermal cycling. In one embodiment of the invention, the primers contain a restriction site 52 that is cleaved 53 into an overhang, or "sticky end" in the final amplicon 51 by the corresponding restriction enzyme. The restriction site can reside within the target-specific domain itself, or it can be introduced completely or in part as an extension on the 5' prime end. A second oligonucleotide, called a linker oligo herein, contains a 3' end 50 that is complementary to the amplicon overhang and a 5' end 49 modified with a reactive species for incorporation into the gel matrix 56 via polymerization. In one method of the invention, the reactive species is an acrylate, however the invention is not limited in this regard. Any reactive species capable of chemical or physical incorporation into a gel is considered by the invention, and the invention is not limited to any particular 5' or 3' orientation. A DNA ligase is added to heal the single strand break 54 that remains after hybridization of the amplicon to the linker oligo 55, covalently bonding one strand of the amplicon 57 to the gel matrix via the linker. The invention is not restricted with regard to the timing of, nor the order of, the addition of the linker oligo, the restriction enzyme, and the ligase. Best practices dictate that if the active group on the linker oligo is substantially unstable at high temperature, the linker oligo should be added after thermal cycling, although the invention is not limited in this regard. Also, the attachment of the amplicons should occur before a substantial amount of the amplicons escape the particles. Otherwise the amplicons may mix between particles, undermining the goal of entrapment. However the invention does consider that perfect entrapment is not necessary for all applications and some degree of mixing can be tolerated. An extra advantage of separating linker attachment from amplicon incorporation is that the linkers can be added at higher concentration, and when combined with the smaller size of the linkers, can yield higher loading of the gel matrix with linkers than otherwise accomplished by direct incorporation of amplicons. Afterwards, amplicon ligation is an efficient process. This two-step approach overcomes the potentially lower efficiencies typical of incorporating longer chain length polymers.

Methods of the invention also comprise non-covalent methods of amplicon attachment to particles, including but not limited to ionic interactions, hydrophobic interactions, and passive entrapment of amplicons within the hydrogel matrix. In certain embodiments the pore sizes of the hydrogel are sufficiently small that amplicons become irreversibly entwined within the hydrogel matrix for the duration of subsequent characterization. Some fraction of the entrapped amplicons will be solvent accessible, in part, allowing further biochemical characterization. In other embodiments of the invention the amplicons are further modified to promote entrapment, such as oligomerization, circularization, branching, or other self-assembly into complicated morphologies.

Figure 10:
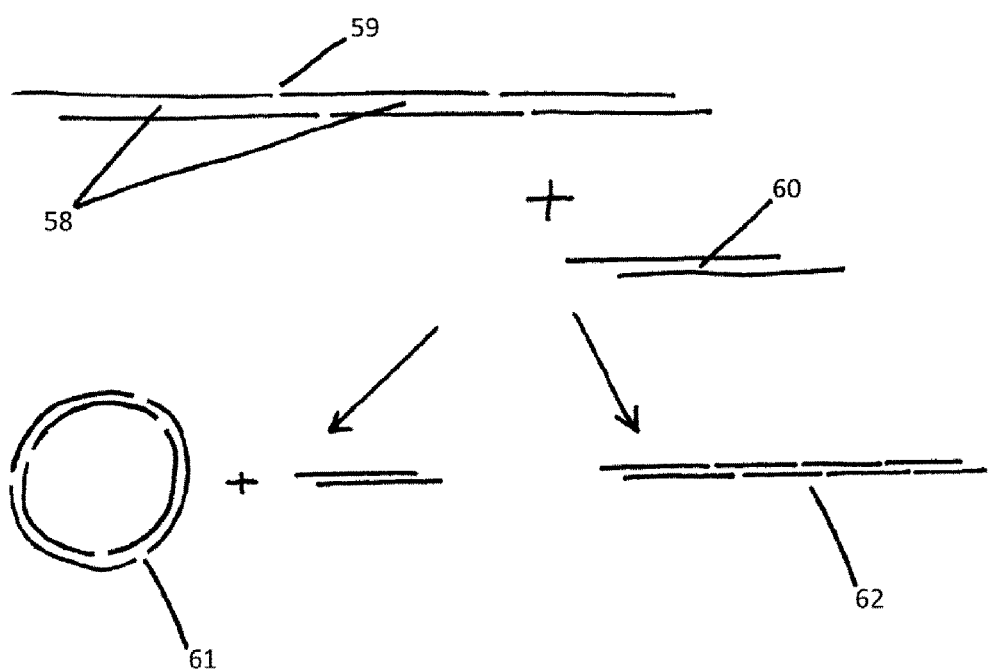
FIG. 10 shows DNA concatemerization or circularization.

In one method of the invention, both primers contain restriction sites, and during or after PCR the corresponding restriction enzyme cleaves the ends of the double stranded DNA leaving overhangs. As with the linker oligos above, the restriction sites can reside in the target-specific region or be introduced fully or in part as an extension to the 5' end. In this method of the invention, the restriction sites are selected such that the overhangs on either end of a single molecule are self-complementary, assured by selecting the same palindromic restriction enzyme for both sites. Illustrated in FIG. 10, self-complementarity opens the possibility of circularization 61, however short amplicons 60 on the order of 100 to 200 bp long are semi-rigid, being substantially similar in length to the persistence length of duplex DNA. Hence these molecules resist the first order reaction of internal circularization allowing instead for second order concatemerization 62. Chain growth continues until the macromolecule achieves sufficient flexibility for circularization. Afterwards, during gel polymerization, the growing chains comprising the gel matrix can entrap the concatemerized amplicons, sometimes passing through the center of circularized amplicons trapping them permanently although not covalently.

Internal circularization limits the size of simple amplicon concatemers. In one method of the invention, a fraction of the primers do not form overhangs and they are mixed with the majority of the primers that do, producing what are called blocked ends herein. Illustrated in FIG. 13, the infrequent blocked end 76 prevents concatemer growth in one direction and serves as a seed point for linear chain growth 77 by inhibiting circularization. The optimal fraction of blocked ends is a balance between inhibiting circularization and introducing chain termination at a second blocked end, and it depends on the concentration and the length of the amplicons. Higher amplicon concentrations favor linear growth allowing a lower fraction of blocked ends, whereas longer amplicons are more flexible and hence prone to circularization, favoring a larger fraction of blocked ends. In another method of the invention, amplicons self-assemble into even larger branched structures by annealing to small multivalent "unions" 78. As above, restriction digestion produces the amplicon overhangs via sites introduced with the primers. In one embodiment, the restriction sites are different preventing immediate internal circularization, however the invention also considers self-complementary overhangs. Illustrated in FIG. 12A, the unions are small duplex DNA structures with internal self-complementary regions 73 and with overhangs 72 complementary to those on the amplicons. The single strands 71 comprising the unions should be long enough for stable annealing to each other at room temperature—at least 8 base pairs—plus extra for the overhangs, but no longer than the amplicons to avoid hindering the kinetics of concatemerization. In the simplest embodiment, the unions comprise two strands with two overhangs, bridging pairs of amplicons for linear concatemerization. It is understood that the overhangs on the unions may be filled in during extension in PCR, however when the unions contain the same restriction sites as their matching amplicons then overhangs of the unions will be refreshed or created for the first time during the same restriction digestion that provides the overhangs of the amplicons.

In other embodiments of the invention the unions have three or more overhangs, as shown in FIG. 12A. These more complicated three dimensional DNA structures are well known to those of ordinary skill in the art, and include Y-shaped and X-shaped DNA formed from three or more separate DNA strands, although the invention is not limited in this regard. Any macromolecular structure capable of bridging two amplicons is considered by the invention including but not limited to LNA, PNA, RNA, and any hybrids thereof; and protein systems such as streptavidin-biotin and digoxigenin-antibody complexes. Mixtures of different types of unions are also considered by the invention to control the extent of branching and looping during concatemerization. The invention also considers blunt-end ligation of amplicons either to themselves and/or to unions.

Without wishing to be bound by any particular biochemical arrangement, the overhangs from restriction digestion are typically too short for stable annealing at room temperature. Hence, in the preferred embodiment the emulsion mixture also contains a ligase to covalently bind the amplicons and unions into large nanoscopic or even microscopic DNA structures. As above with linker attachment, the invention is not limited in regard to the timing or the order of operation of addition of the unions, the ligases, and the restriction enzymes, although generally restriction enzyme digestion precedes ligation. The invention also includes methods whereby if the DNA structures are sufficiently large and stable, the formation of an extra hydrogel scaffold is not necessary and the "DNA hydrogel" is sufficient for downstream physical and biochemical characterizations. In one method of the invention, the emulsion is dehydrated to increase the density of the DNA hydrogel. Any dehydration method is compatible with the invention, including but not limited to exposing the amplified droplets to a second population of droplets that are hypotonic compared to the amplified droplets. Osmotic pressure then drives a flux of water from the amplified droplets to the "dryer" droplets through the oil phase, most likely via surfactant micelles but also directly across the surfactant bilayers between adjoining droplets in emulsions largely drained of oil.

Figure 11:
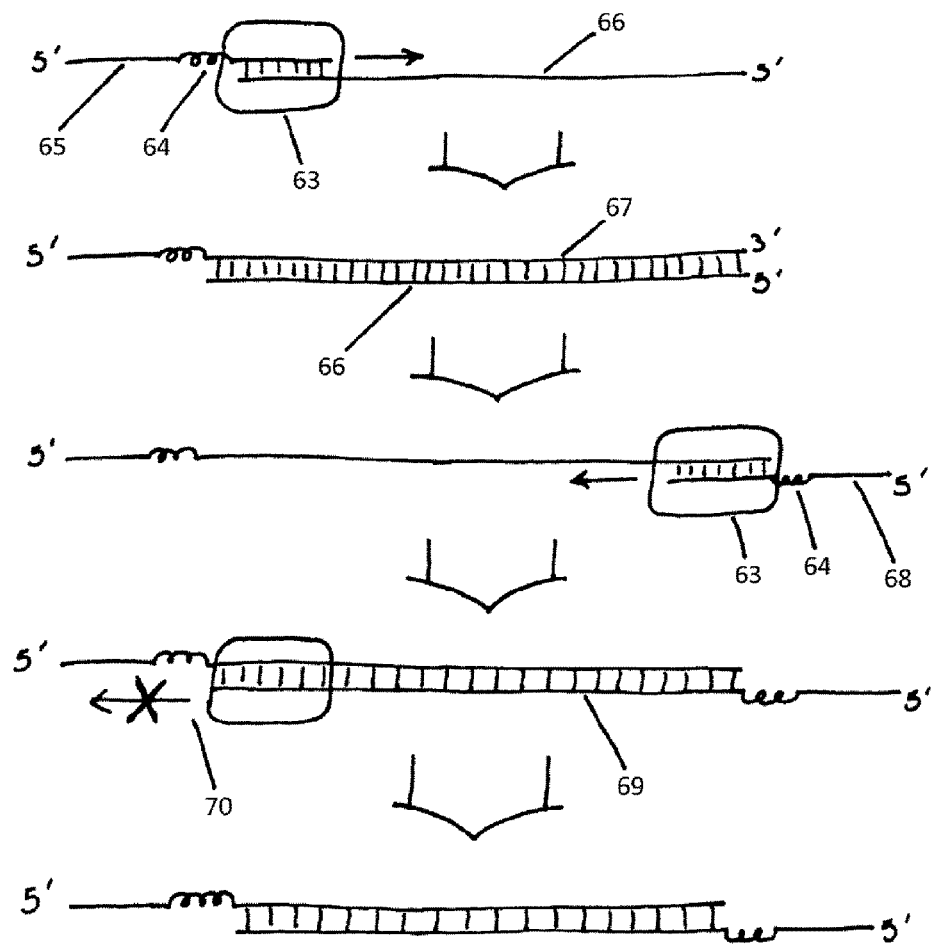
FIG. 11 shows amplification of DNA leaving overhangs.

In an alternative method of the invention to ligation, self assembly at room temperature drives the formation of large branched and/or unbranched DNA concatemers from amplicons and unions, if required. The complex structures are stabilized at room temperature without covalent attachments by increasing the length of the sticky ends and/or switching to tighter-binding DNA analogs, eliminating the need for ligation in the above methods. Illustrated in FIG. 11, in certain methods of the invention, the higher affinity overhangs are incorporated into the amplicons with primers containing three domains: a 3' domain specific for target DNA 66 for primer extension, a 5' attachment end 65 that is either self-complementary to the 5' end of the opposite primer or complementary to a union, and a domain spanning between the two 64 that is not replicable by the polymerase 63, called a blocking domain. The blocking domain stalls 70 the polymerase, preserving the overhang as originally designed instead of obstructing it with matching base pairs, requiring subsequent restriction digestion. This method of the invention allows flexible engineering of the overhang through oligo synthesis, as opposed to limiting the configurations to cleavage patterns from known restriction enzymes. Many polymerase blockers are known to those of ordinary skill in the art, including but not limited to alkyl group such as C3 spacers; photocleavable spacers; polyethylene glycol spacers; nucleotides with alternatives bases, or substituents, or lacking a base; and LNAs and PNAs. In certain embodiments, the blocking domain overlaps partially or completely with the attachment domain. In these embodiments, the non-native nucleotides or analogs, such as LNA and PNA, block the polymerase but retain the ability to bind selectively with a counterpart on an opposite strand. The invention considers any attachment chemistry capable of selectively or non-selectively binding together two overhangs subject only to the restriction that the chemistry should not inhibit DNA amplification or disrupt the emulsion.

The target-specific domain of these tripartite primers is designed according to standard primer design guidelines well known to those of ordinary skill in the art, and the attachment domain is designed by similar guidelines, also well known to those of ordinary skill in the art, to maximize affinity for the complementary strand while not impeding PCR. In general the full primer construct should have minimal secondary structure that would otherwise compete with the intended interactions, and the melting temperature of the attachment domain to its counterpart should be lower than the annealing/extension temperatures of PCR, but otherwise as high as possible above room temperature for stable concatemerization. Note that undesirable formation of primer-dimers is not an issue for these primers due to the blocking domain, despite any self-complementarity between the attachment domains. In certain embodiments the overhangs are self-complementary and concatemerization occurs spontaneously between amplicons. In other embodiments unions bridge non-complementary ends, as described above.

Figure 12:
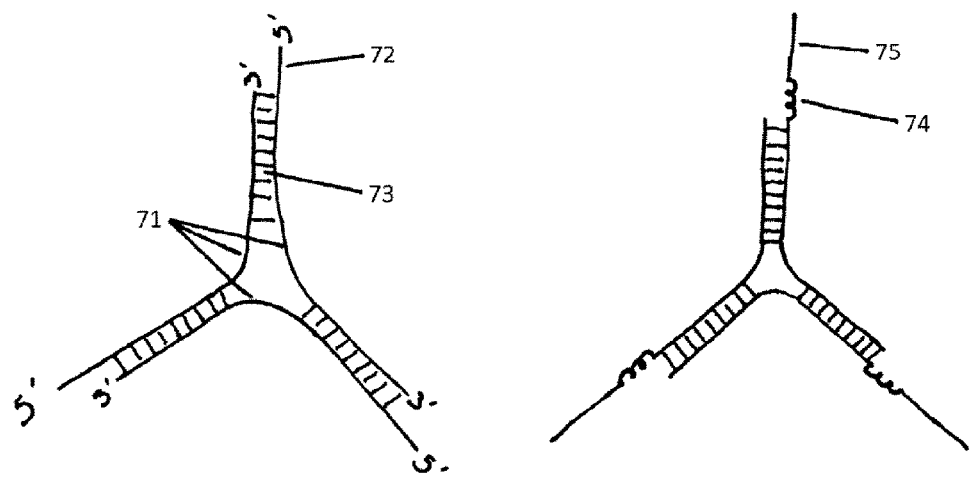
FIG. 12 shows self-assemblies of DNA oligos leaving three overhangs.
Figure 13:
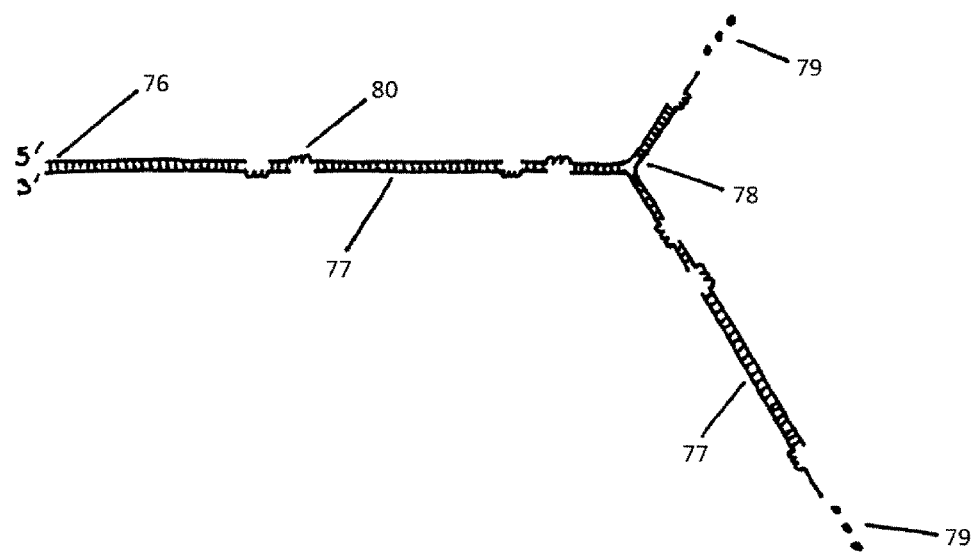
FIG. 13 shows DNA concatemerization with an end block and a union.

The desired complexity of the self-assembled structures can be tuned with end blockers and unions in the same manner as described above for the case of adhesion through restriction digestion and ligation. As illustrated in FIG. 12, one construct for compatible unions adopts the same tripartite structure as the primers with a non-replicable blocker 74 protecting the overhang 75 for attachment. Briefly, complexity increases roughly in the order of the following configurations: (low) self-complementary primers yielding small circular concatemers, (middle) non-complementary primers including end blocks connected with divalent unions that yield longer linear molecules, and (high) the previous condition plus X- and Y-shaped unions that yield complex branched molecules. One advantage of self-assembly is that the size of the amplicon complexes can be tuned without disrupting the reaction conditions for PCR. It is generally accepted that 5' modifications to PCR primers has negligible effects on PCR efficiency, provided that the typical primer design guidelines known to those of ordinary skill in the art are followed. Also, provided that the melting temperatures of the union attachments are substantially below the annealing/extension temperature of PCR, and also provided that the interior regions of the unions are properly designed with negligible sequence homology to either the targets or any background DNA, the unions can be introduced with the PCR mixture before emulsification. Alternatively, the unions can be introduced afterwards on a droplet-by-droplet basis by methods of the invention described above. In either method, the unions only exert their impact once the temperature returns below the melting temperature of the attachments.

Amplicon concatemerization proceeds by a step-growth polymerization mechanism with well understood reaction kinetics. One advantageous characteristic of this mechanism is the rapid loss of monomers and low molecular weight polymers throughout the solution. Hence uniform entrapment can be achieved with high efficiency. In contrast, the incorporation efficiency with covalent methods, such as with Acrydite™ modified primers, is known to decrease as a function of the length of the nucleic acid. Additionally, amplicon concatemerization is completely reversible by melting the attachments at higher temperature, useful in later stages for amplicon release from particles and for accessibility to hybridization probes.

In one aspect, the invention is an article. In one embodiment, the article is a gel droplet comprising two materials: a conventional hydrogel scaffold with entrapped nanoscopic or microscopic DNA concatemers. The DNA concatemers are formed by methods of the invention above, resulting in a high yield of DNA entrapment within the conventional hydrogel scaffold. The scaffold co-localizes the DNA concatemers, and it controls the DNA release when the concatemers are disrupted. In another embodiment, the article is the same as above except the DNA is chemically or biochemically functionalized by any of numerous methods known to those of ordinary skill in the art. As one non-limiting example, one end of a union may contain a biotin, and after concatemerization and gel polymerization, the gel droplet is exposed to streptavidin and another biotinylated biological macromolecule such as an enzyme. The enzyme is captured as it diffuses into the gel by the DNA-biotin-streptavidin complex. Thus, in this embodiment of the invention the article is a hydrogel scaffold exhibiting efficient and readily reversible enzyme capture, however the invention is not limited in this regard. The particles can be reversibly functionalized in this manner with any chemical or biochemical molecules.

In another aspect of the invention, the same biochemical strategy using tripartite primers to enable non-covalent concatemerization described above can also be used for non-covalent attachment to the gel matrix with the linker strategy described further above. In this method of the invention, as above, the amplicons are incorporated with long overhangs or overhangs with base analogs that survive polymerase extension due to the blocker. On the 3' end, the linkers contain the complementary domain for attachment to the amplicons, and as described above, a chemically active modification on the 5' end for direct covalent incorporation into the growing hydrogel during polymerization. In this manner the amplicons are captured onto the gel by hybridization to the linkers, a readily reversible process.

In one embodiment of the invention complete polymerization of the gel precedes DNA amplification. The invention considers passive entrapment of the amplicons in this case using any of the methods described above, including both covalent and non-covalent amplicon concatemerization.

Illustrated in FIG. 6, once the hydrogel particles have been formed and the amplicons are incorporated into the gel 40, the particles are separated from the oil 41 by any means, but typically by repeated washing with DNase free buffers. The particles are further washed to remove all unbound components including the unreacted components of the PCR and prepolymer mixtures, as well as any original DNA from the sample and unbound or untrapped amplicons. Immersion with low osmolarity permselective solutions, such as high molecular weight PEG, dehydrates the hydrogel particles, a readily reversible process by re-immersion into standard buffers. This flow of water into and out of the particles facilitates deep washing by flushing the internal pores akin to squeezing a sponge.

In practice, the extent of particle cleanliness depends on the application, but the particles are generally clean for most intents and purposes after two washes with PEG solution and two washes with buffer.

The purified particles ideally contain only bound or entrapped amplified clonal DNA, and are referred to as DBs (DNA beads) from this point forward. Methods of the invention include any chemical, biological, biochemical, or physical characterization of the DBs. In certain methods of the invention, the DBs are characterized to identify rare genetic variants with very high sensitivity and specificity in a multiplexed assay format. In the preferred embodiment, the first step is to physically separate DBs containing the rare DNA types, or genotypes, and the second step is to identify the genotypes.

Figure 7:
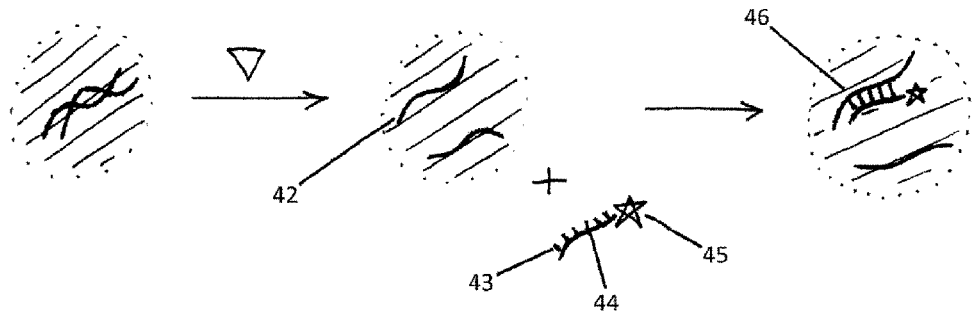
FIG. 7 shows sequence analysis of gel encapsulated DNA by hybridization.
Figure 8:
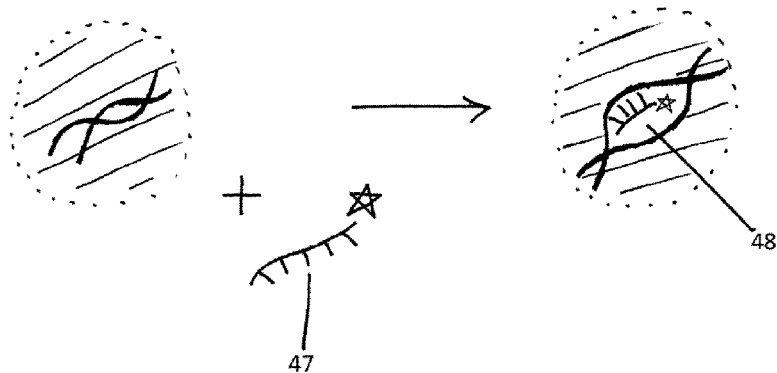
FIG. 8 shows sequence analysis of gel encapsulated DNA by a strand-invading hybridization probe.

Many methods for probing DNA sequence are known to those of ordinary skill in the art, including dynamic allele specific hybridization (DASH), restriction fragment length polymorphism, invader assay, primer extension, 5' nuclease assay, molecular beacons, high resolution melting analysis, DNA mismatching binding proteins, and the oligonucleotide ligation assay. However the invention is not limited in this regard. Any method for probing DNA sequence is considered by the invention. However the preferred technique is straightforward hybridization 46 of DNA oligonucleotide probes with fluorescent labels, illustrated in FIG. 7. In one method of the invention, the probes against the rare DNA targets 43 have distinguishable fluorescent colors 44 compared to probes against the abundant DNA targets, if present. In cases that the abundant targets differ from the rare ones by only one or a few nucleotide bases, probes against both target types are generally included to prevent non-specific binding. However, in cases that the rare types are substantially different from all other genetic material in the sample, then probes against the abundant types might be unnecessary. DNA hybridization techniques are well known to those of ordinary skill in the art, including general guidelines for high stringency hybridization such as higher temperatures, lower salt concentrations, and proper probe design. Methods of the invention employ these techniques to achieve high specificity hybridization of the probes to the bound DNA. In certain methods of the invention, the DBs are first heated under mechanical agitation to temporarily dissociate or completely wash out the complementary strands of the amplicons bound to the particles. The bound strands 42 remain. Otherwise, hybridization efficiency might be low on account of competition between the hybridization probes and the unbound complementary amplicon strands. In other methods of the invention this step is unnecessary, including but not limited to DBs fabricated by asymmetrical PCR that yields more of one strand than the other or hybridization probes designed for strand invasion 48 such as LNA and bis-PNA probes 47, illustrated in FIG. 8. Specialized probes, such as molecular beacons, are considered by the invention for improving specificity. Molecular beacons also eliminate the need for washing the DBs after hybridization, an otherwise desirable step to remove any non-hybridized probes.

After hybridization and washing, the DBs with the rare DNA type are either identified or sorted from the empty beads and the beads with the abundant DNA type on the basis of fluorescence color or any other fluorogenic or light scattering property of the DBs. Various methods of sorting fluorescent beads are known to those of ordinary skill in the art, and all are considered by the invention, but the preferred method is by fluorescence activated cell sorting (FACS). Most FACS vendors support a high throughput exceeding $10^4$ beads per second with a capability of dispensing individual beads into separate wells of a microtiter plate for further analysis. In this manner, small numbers of DBs containing the rare genotypes can be rapidly sorted from millions of beads in total to achieve very high sensitivities. In multiplexed assays, the collected pool of DBs will contain some or all of the different rare targets, plus perhaps a few false positive beads with the abundant DNA type. In a critical aspect of the invention, the beads can be further characterized to identify the different rare targets as well as providing a second stage to exclude false positives.

Characterization of the small number of collected DBs can be performed in myriad ways, and all are considered by the invention. Methods of the invention include but are not limited to sequencing, hybridization, protein binding, and restriction digestion. Any method for identifying the DNA sequence captured on the DBs is considered by the invention, and the best method depends on the application. For assays with a small number of targets, direct hybridization may be the best strategy. In this method of the invention, the DBs are washed and exposed to one or more target-specific hybridization probes, again including blocking probes to avoid non-specific binding to similar sequences as necessary. A number of targets can be probed simultaneously, limited only by the number of distinguishable signatures of the probes. When the detection method is conventional fluorescence imaging, the maximum number of probes is typically four or five due to the confined spectral space and the relatively broad fluorescence emission profiles; however the invention is not limited in this regard. There are various specialized techniques to overcome this barrier known to those of ordinary skill in the art and all are considered by the invention. For assays with more than the maximum number of targets, the DBs can be characterized with multiple sets of probes in a serial operation.

In another method of the invention, the DBs are characterized by DNA sequencing. Not wishing to be bound by any biochemical arrangement, the input sample for sequencing is generally free DNA unbound to any surfaces. In certain embodiments, a secondary PCR is used to amplify DNA off of the DBs. For single plex assays the original primers suffice for further amplification. However, for multiplexed assays the identity of the DBs may be unknown. In one embodiment of the invention, the original sequence-specific PCR primers may contain universal primer sites. In the case that linker oligos are used, the universal primer site may overlap with the linker recognition site, or it may be sandwiched between the linker site and the target recognition site. Alternatively, a mixture of target specific primers can be used in a multiplexed PCR. Generally multiplexed PCR poses challenges like DNA bias, however in certain methods of the invention such challenges are mitigated by isolating the DBs from each other during secondary amplification thereby presenting only one target for each individual amplification with little or no background DNA. Additionally, the target specific primers may or may not be the same as the original primers. In the case that they are partially or completely different—often called nested PCR—the secondary PCR affords another layer of stringency to eliminate false positives arising from similar sequences. The invention is not limited to any of these secondary PCR strategies; rather the invention considers all PCR strategies capable of replicating the bound DNA into a free form.

In other embodiments of the invention, restriction enzyme digestion is used to free DNA from the DBs. In certain embodiments the original PCR primers contain 5' overhangs with restriction enzyme sites not present in the target DNA sequence, thereby introducing the sites into the amplicons. Alternatively, the target DNA may contain suitable restriction sites. Many restriction enzymes are known to those of ordinary skill in the art, and all are considered by the invention. When the restriction enzyme sites are incorporated into the primer sequence, the selection of the type of restriction enzyme must take into account the surrounding DNA context and abide by the common primer design guidelines well known to those of ordinary skill in the art.

For certain DNA sequencing techniques, like Sanger sequencing, most of the input DNA should be substantially similar for clearest results. In these cases the DNA from the DBs should be replicated or fragmented from the beads individually, for example with one bead per well of a microtiter plate. For other DNA sequencing techniques, including but not limited to next generation 454, Illumina, or Ion Torrent techniques, the DNA from all DBs may be mixed with the results sorted out later during bioinformatics analysis. In certain embodiments of the invention, sample-specific "barcodes" comprising short DNA sequences are included in the original PCR primers. Alternatively, the barcodes can be incorporated into the primers of the secondary sequencing. These barcodes allow pooling of multiple samples into a single next generation sequencing run to reduce sequencing costs.

While the methods of the invention involving microdroplet polymerization have been described in the context of DNA entrapment up to this point, the invention is not limited in this regard. The invention considers broadly the injection of polymerization reagents, in all of the reagent configurations described in detail above, into an incoming stream of droplets. For this purpose injection is defined as the transient merging of a droplet, surrounded by a continuous immiscible phase, with one or more continuous miscible phases during which time some volume of the continuous phases displace into the droplet before the miscible phases are separated again. The microfluidic methods of the invention are preferred for injecting reagents for gelation with polyacrylamide, however the invention is not limited in this regard. Any microfluidic method for injecting prepolymer reagents into droplets is considered, including the methods described above termed lambda- and picoinjection. The invention is not limited with regard to what species may become entrapped in the microgels. Rather, the invention considers the entrapment of any species that either participate in free radical polymerization, thus becoming covalently entrapped, or merely become entrapped by physical entanglement. As non-limiting examples, the invention considers the entrapment of relatively large biological objects that cannot migrate through the gel, such as cells, viruses, spores, pollen, small multicellular organisms, micro- and nanoscopic beads, smaller gel microparticles, large DNA structures like chromosomes and artificial chromosomes, and liposomes. The invention also considers entrapment by limited migration of inorganic material such as fine powders that can be adequately dispersed in solution. The invention also considers the covalent entrapment of smaller species that contain chemical moieties necessary to participate in free radical polymerization, such as vinyl groups, either natively or by through molecular engineering. Non-limiting examples include proteins functionalized with acrydite or other vinyl groups, and any macromolecule with an accessible electron pair.

While the invention has described droplet polymerization so far in the context of injecting polymerization reagents into an incoming stream of droplets, the invention is not limited in this regard. The invention also considers the polymerization of droplets generated by the method of the invention shown in FIG. 3. In this embodiment, the monomers, initiators, and any porogens are injected through the side channels along with any species desired for entrapment. As above, the invention considers the entrapment of any species that either participate in free radical polymerization, thus becoming covalently entrapped, or merely become entrapped by physical entanglement.

In yet another embodiment of the invention, the microfluidic methods of the invention or other similar microfluidic methods are used to quantify nucleic acids by injecting the droplets from an emulsion PCR with DNA capture beads on a one-by-one basis without otherwise disrupting the emulsion. In this method of the invention spatial co-localization of the clonal DNA is retained by immobilizing of the DNA onto microbeads while still isolated within droplets, as opposed to converting the droplets into hydrogel particles. Either the bi-injector microfluidic device of the invention, or any other microfluidic method of droplet merging known to those of ordinary skill in the art, will be used to inject small numbers of beads into droplets without otherwise disrupting the emulsion. The invention considers any DNA-bead binding method known to those of ordinary skill in the art, however certain standard methods for DNA immobilization onto beads, such as streptavidin-biotin binding may not be suitable because the unreacted PCR primers cannot be washed away. Alternative methods such as ligation-rolling circle amplification can overcome such challenges. Once the clonal DNA is co-localized onto beads the emulsion is broken and the beads are washed and interrogated with standard fluorescent hybridization probes or any other method of DNA sequence characterization. Mutant DNA may also distinguished from the wild-type by fluorescence color within a fluorescence activated cell sorter (FACS) and segregated for further sequencing analysis that reveals the type of mutation.

In yet another embodiment of the invention, the methods of the invention for entrapping DNA within gel microparticles are combined with a novel method for analyzing the DNA sequence by hybridization when the exact sequence of the DNA is uncertain. This situation often arises when DNA has mutated within a small locus, such as in variable deletion mutations in exon 19 of EGFR associated with lung cancer. In this method, two hybridization probes are used with different colors. One probe overlaps the variable domain, and another probe overlaps a neighboring conserved domain. The probes have different fluorophores, and color correlation is used to distinguish mutant vs. wild-type. Wild-type particles are dual colored, but mutant particles lack the probe for the variable domain. During particle sorting only the single-color mutant particles are collected. Afterwards the exact mutation is identified by sequencing as above. In this manner, incorporating amplicons into gel particles significantly expands the type of mutations that can be analyzed from the somewhat limited traditional "hotspot" mutations to include variable regions as well. The method is not limited to deletions alone; it will also work with additions and replacements.

Example Applications

Electronics

Figure 14:
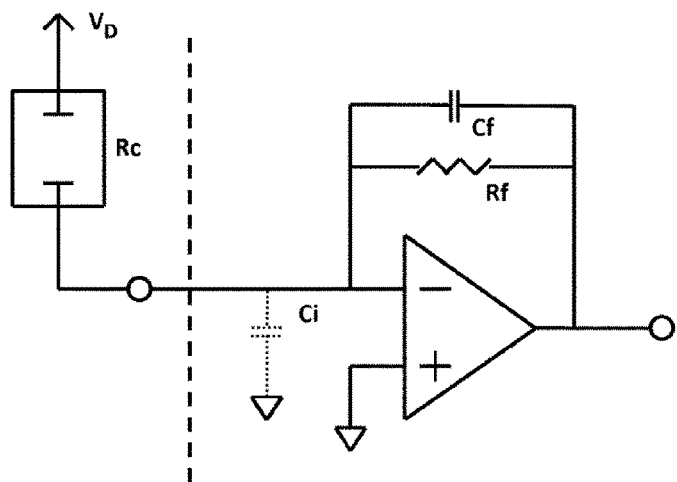
FIG. 14 shows an electronic equivalent circuit of the instrument and microfluidic chip.

To initiate droplet merging and to measure electrolyte continuity with a microfluidic chip, a supply voltage, $V_D$, was applied to one electrode in fluidic contact with a microfluidic injector channel. Another electrode in fluid contact with the other injector channel was connected to the input of the amplifier shown schematically in FIG. 14. The amplifier was configured as a current-to-voltage converter that asserts a "virtual" ground at the input, a configuration known well to those of ordinary skill in the art. Hence the full voltage applied across the microfluidic device equaled $V_D$. $V_D$ was powered from a linear DC supply (GPS-3030D, Instek) typically operating in the range between 5-20 V.

The conductivity of the electrolyte within the microfluidic channels was estimated as a guide for conditioning the electrical signal for droplet detection. A 50 mM NaCl solution was assumed for the model, with a 1.8Ω·m conductivity. The geometry of a prototypical microfluidic design was approximated as three rectangular sections: a microfluidic junction, an upstream entrance to the junction, and a large connector to a remote chip port (width, length, and height of 50 µm, 50 µm, 50 µm; 500 µm, 1000 µm, 50 µm; and 1000 µm, $10^4$ µm, 200 µm respectively), for a total predicted resistance on the order of 200 kΩ. This order of magnitude assessment of the resistance within the microfluidic chip guided the selection of the feedback resistor in the current-to-voltage converter used for current monitoring, as follows.

Figure 15:
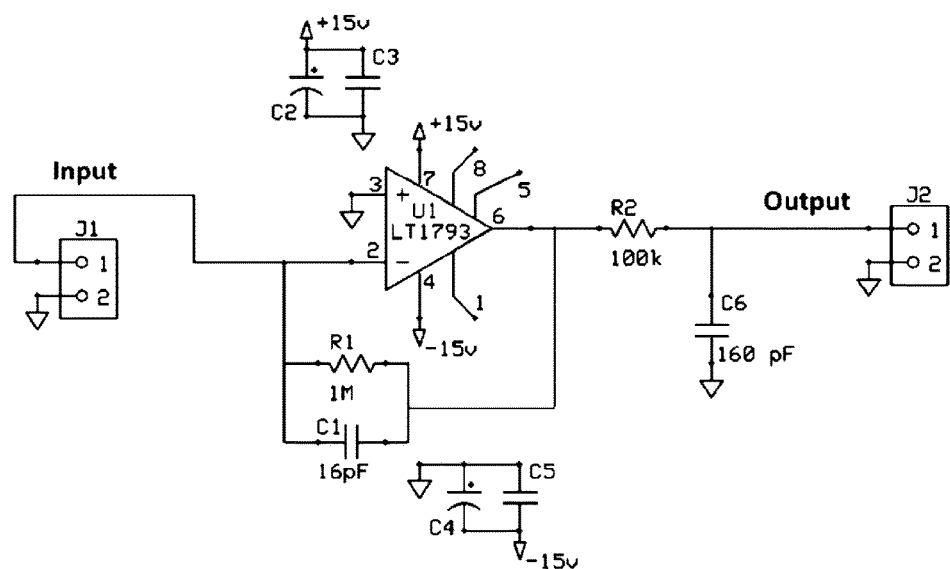
FIG. 15 shows a transimpedance amplifier.

FIG. 15 shows the current-to-voltage converter circuit used to measure conductivity changes within the microfluidic circuit. A high speed operational amplifier with low noise and low input bias current (LT1793, Linear Technology) was arranged in the typical transimpedance configuration known well to those of ordinary skill in the art. The amplifier was bypassed with 4.7 and 0.1 µF parallel capacitors on each supply input, supplied with a 1 MΩ feedback resistor, and compensated for stable operation with a 16 pF feedback capacitor. While performing as a typical current-to-voltage converter, due to the high electrical resistance within the microfluidic device, the frequency response of the complete circuit including the microfluidic device actually behaved as a feedback amplifier in the inverting configuration (see FIG. 14) with a constant input "signal" of $V_D$ and a gain that varied with changing resistance $R_C$ (the resistance of the microfluidic chip). Nevertheless, the first pole that dominated the frequency response arose from the feedback components, $R_f$ and $C_f$, with a predicted roll-off at ~10 kHz. Higher frequency responses could be obtained with more aggressive selection of $C_f$, reduced feedback resistance, and selection of a faster amplifier, but with a possible tradeoff of reduced signal-to-noise ratio. As shown in the droplet detection data below, the signal-to-noise ratio was quite high allowing ample headroom for higher frequency responses as necessary. Hence the ~10 kHz response demonstrated here is not limiting for the invention. Significantly faster responses are anticipated.

A second low-pass RC filter was appended to the amplifier output, also with a 10 kHz roll off, to account for noise gain from the amplifier input. Noise appearing at the inverting input is amplified on account of the non-unity feedback fraction. The parallel paths to ground from the inverting input through the microfluidic channel, $R_c$, and through the input capacitance of the amplifier, $C_i$, attenuate the feedback of the noise signal. Due to the series capacitances, $C_f$ and $C_i$, the noise amplification survives at frequencies above the $R_f C_f$ roll-off for the signal. Hence the second filter is recommended for highest signal-to-noise performance, but it is likely that the circuit would perform adequately without the second stage filter in certain circumstances for droplet detection. Hence the invention is not limited in this regard. Furthermore, the invention considers any electrical method suitable for measuring conductivity changes, including but not limited to measuring the voltage across a simple resistor as a current measuring device.

Microfluidics

The microfluidic devices were fabricated with standard soft lithography, a process well known to those of ordinary skill in the art. In brief, SU-8 (2050, Microchem) was spin coated to a nominal 50 µm thickness on a polished silicon wafer and photopatterned using a transparency mask (Cad/ART) and a mask aligner (MJB4, SUSS MicroTec). Spin coating, UV exposure, and pattern development were all carried out according to manufacturer instructions for SU-8 in a clean room environment. The resulting patterned wafer was used as a molding master for polydimethylsiloxane (PDMS) (Sylgard 184, Dow Corning) using vacuum degassing to remove any air bubbles from the uncured PDMS on the master surface. The PDMS was cured at 65° C. for 2 hrs, ports for fluidic access were cored through the cured PDMS with a 0.5 mm biopsy punch (Robins Instruments), and then cover glass was bonded immediately following plasma activation of both the PDMS and the cover glass. 1H,1H, 2H,2H-perfluorodecyltrichlorosilane (Alfa Aesar) in FC-3283 (3M) (1:100 v/v) was driven through the chip by a syringe pump (14-831-200, Fisher Scientific) and washed out with ID oil (see oil composition below) to create a hydrophobic surface suitable for generating and manipulating water-in-oil emulsions.

Two microfluidic designs were demonstrated, one for droplet generation and the other for droplet merging. For simplicity, the first design is called the droplet generator throughout, and the second design is called the bi-injector throughout. However each design was demonstrated performing both functions. Such naming does not imply any limitation in the invention.

Figure 16:
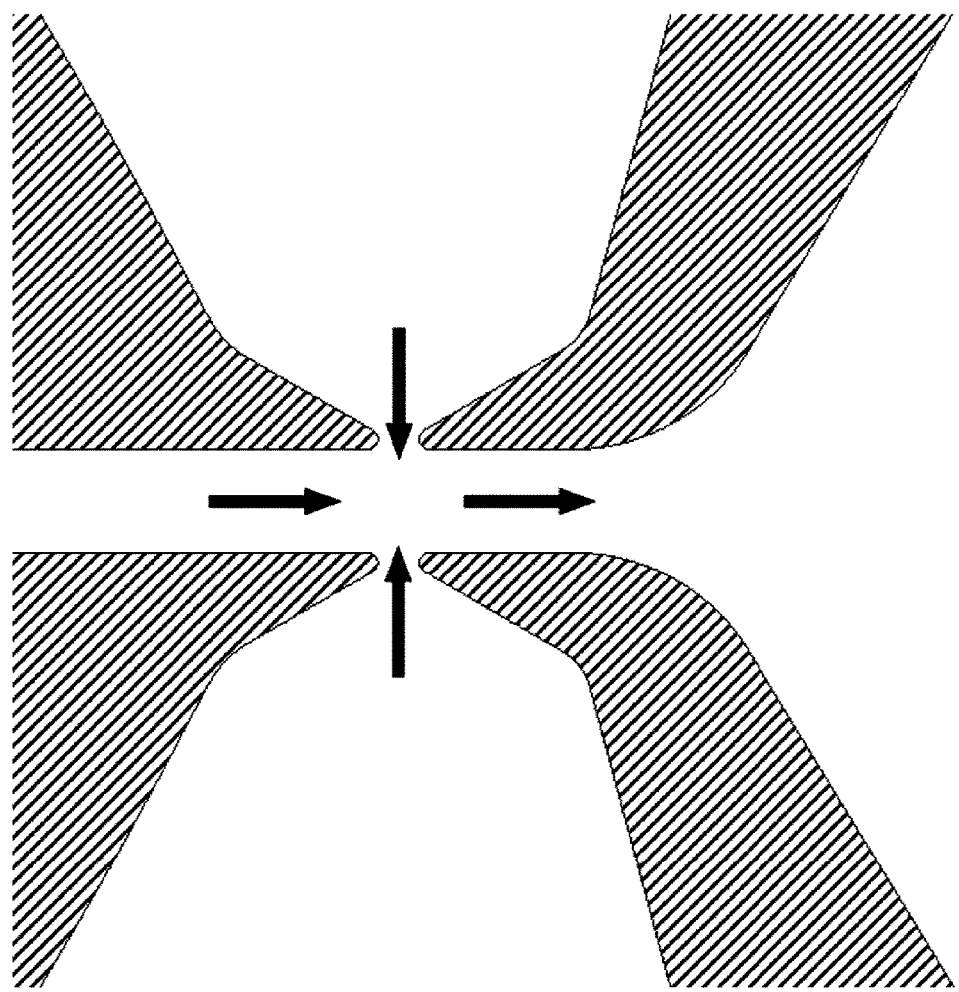
FIG. 16 shows a microfluidic circuit.

The droplet generator is shown in FIG. 16, comprising four channels intersecting at one location. Fluid delivery from the outside ports cored through the chip to this intersection was accomplished by techniques well known to those of ordinary skill in the art. Access channels with relatively large cross-sections spanned the distance from the ports to the intersection to limit both hydrodynamic and electrical resistance, the latter when applicable. The channel depths throughout the device were nominally 50 µm. The width of the main channel entering the intersection from the left in FIG. 16 was 50 µm, and the narrow orifice of the injector channels entering the intersection from the top and the bottom was 20 µm. The intended flow direction within each channel is indicated by arrows in FIG. 16. For droplet generation with this device, a continuous oil phase is driven into the intersection from the left channel, and two continuous aqueous phases are driven from the top and bottom channels into the intersection. The mixed phase fluid emerged from the intersection in the channel to the right.

The aqueous channels feature an abrupt taper entering the intersection. The wide channel up to the sudden constriction minimizes the hydrodynamic and electrical resistance of these channels, particularly important for maximizing the electrical signal-to-noise measurement for droplet detection, but also important for maximizing aqueous injection rates in certain modes of operation. The output of the intersection features an abrupt opening that provides a low hydrodynamic resistance to the exit port. While not necessary for device operation, the low downstream resistance minimizes cross-talk between flow in the different upstream channels when controlling the flow rates with a fixed pressure boundary condition. In brief, minimizing downstream resistance reduces any pressures changes at the intersection caused by changing the flow within any of the input channels. For instance, increasing the oil flow rate from the left in FIG. 16 will raise the pressure at the intersection. Under the fixed pressure condition, the overall pressure drop across the top and bottom aqueous channels will decrease with increasing pressure at the intersection, reducing the flow through these channels. The extent of this cross-talk depends on the relative upstream and downstream resistance. Lowering the downstream resistance for this examples does not imply any limitation in the device. Higher downstream resistances can be readily accommodated by any of a number of methods well known to those of ordinary skill in the art, including but not limited to corrective resistor modeling and fixed flow rate boundary conditions. In certain instances higher downstream resistances can be advantageous. For example, a relatively long channel of similar width to the exit channel may be included in the design to allow the surfactant from the oil time to mature at the water-oil interface of the droplets.

Figure 17:
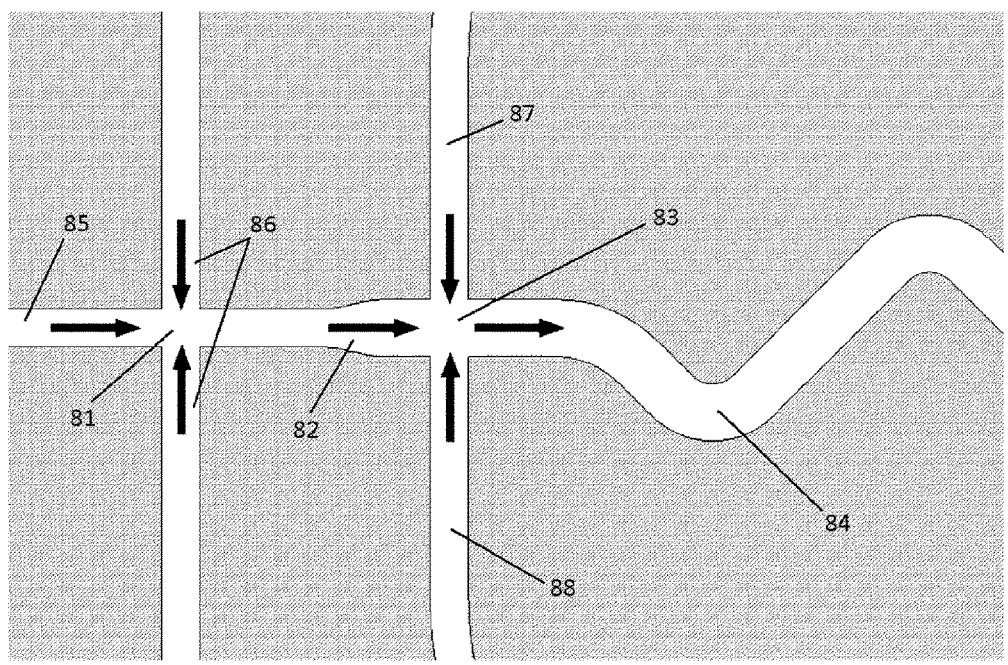
FIG. 17 shows a microfluidic circuit.

FIG. 17 shows the bi-injector 83 microfluidic design with an extra upstream feature 81, for either droplet generation or for reinjection of an emulsion, and a downstream serpentine mixer 84. Arrows in FIG. 17 indicate the intended flow directions. The channel widths 85, 86, 87, and 88 were 50 µm and downstream from the flare 82 widened to 75 µM entering and then leaving 84 the bi-injector 83. The target channel depth was uniformly 50 µm throughout the microfluidic layer. As with the previous design, low resistance access channels connected these channels to the outside ports of the chip.

The bi-injector 83 receives an incoming stream of droplets from the left in FIG. 17 that originates from the upstream 'X'-shaped feature that can either function as a droplet generator or an emulsion reinjector. This microfluidic structure is well known to those of ordinary skill in the art, but briefly, in both modes a continuous oil phase arrives at the intersection 81 from top and bottom channels 86. In droplet generator mode a continuous aqueous phase enters the intersection 81 from the left channel 85 and is dispersed into a stream of uniformly sized droplets spaced apart by oil. The dispersion of the aqueous phase arises from fluid strain within the intersection 81 overcoming the surface tension of the bolus of aqueous phase that periodically protrudes into the intersection. In the mode for emulsion reinjection, a packed water-in-oil emulsion is driven into the intersection 81 from the left through the channel 85. The cross-section of the reinjection channel 85 is intentionally sufficiently small—on the order of the equatorial cross-section of the droplets—such that the droplets within the emulsion arrive in single file into the intersection 81. In this mode, with properly poised flow rates, the droplets arriving into the intersection 81 survive the fluid strain within the intersection and emerge intact but separated from each other by a slug of oil from channels 86. While the upstream 'X'-shaped feature 81 has been described alternatively as either a droplet generator or an emulsion reinjector, it is understood that its function is not limited to these roles. Any method of operating this feature such that it delivers droplets spaced by oil into the downstream bi-injector 83 is considered by the invention. As one alternative example, droplets from a packed emulsion arriving in 81 may be split into even smaller droplets by the fluid strain within the intersection. This hybrid device performs both emulsion reinjection and droplet generation simultaneously, and is generally known as a droplet splitter to those practiced in the art. Furthermore, the feature 81 itself is not necessary to support the invention. Any method of delivering a stream of aqueous droplets dispersed within a continuous phase of oil is considered. For the non-limiting example demonstrated here, the feature 81 was operated in droplet generation mode as follows further below.

In the example here the channel leading from 81 widens before entering the bi-injector 83. While this flare in the channel is unnecessary for bi-injector operation, it can facilitate the injection of larger volumes from the side channels within the injector. Without wishing to be bound by any theory, the range of droplet sizes that can be generated within a microfluidic intersection—whether 'X'-shaped or 'T'-shaped or otherwise—generally scales with the size of the intersection. Thus, without the flare it is anticipated that the maximum volumes injected from the side channels into arriving droplets would be smaller under otherwise similar operating conditions. In other words, the flare is intended to increase the volume fraction of the injected fluids within the final merged droplets, a performance property called the "injection capacity" from this point forward.

Continuous aqueous phases arrive at the bi-injector intersection 83 from the top and bottom channels 87 and 88 in FIG. 17. The mouth of these injector channels (also called side channels herein) at the intersection 83 was widened in this design to 50 µm from 20 µm in preceding design (FIG. 16), also with a design goal of achieving a larger injection capacity. The combination of the flare 82 and the wider channels 87 and 88 succeeded in improving injection capacity. The device in FIG. 17 routinely yielded volume fractions of injected fluid exceeding ⅔ of the total volume, whereas the device in FIG. 16 struggled to approach even half of the final volume (data not shown).

In one non-limiting application of the bi-injector considered by the invention, the injector channels contain separate solutes that react on mixing once merged into a droplet. The serpentine feature 84 was appended downstream to facilitate droplet mixing and as a consequence to accelerate reactions or make them more uniform. This microfluidic feature is well known to those of ordinary skill in the art.

Instrumentation

In the following non-limiting examples, flow was driven within the microfluidic chips by fixed pressure. Fixed pressure is generally preferred for droplet applications because fluid "pulsing" evident in other methods, such as from syringe pumps, is minimized or eliminated. However the invention is not limited in this regard. Any method of driving flow is considered, but especially including using fixed flow rate because in certain situations the application may require a high downstream hydrodynamic resistance. In these cases, the tradeoff between flow stability and cross-talk (described above) may favor the fixed flow rate condition instead. In the examples here the downstream resistance was sufficiently low that fixed pressure was preferred. Also, a fixed pressure is often much less expensive to implement.

The different fluids driven into each port of the microfluidic chips were loaded into standard 1.8 mL cryogenic tubes (ArcticIce, USA Scientific). First the caps of these "cryovials" were drilled to accommodate two tubes and optionally an electrode wire, then the tubes and wires were inserted to an appropriate depth, and finally the assembly was sealed with a generous amount of common 5 minute epoxy (Devcon). One of the tubes (1/32" ID, 1/16" OD, PTFE) entering each cryovial was the pressure source, connected on one end to the pressure manifold and terminated on the other end in the airspace above the fluid in the cryovial to avoid any bubbling. The other tube delivered the pressurized fluid to the chip, terminated on one end at the bottom of the cryovial within the fluid, and press-fit into the cored ports of the PDMS microfluidic chip on the other end. The electrode wire, when present, was platinum and protruded enough above the cap to clip to a standard electrical connector. On the other end the electrode was immersed in the electrolytic fluid within the cryovial for electrochemical contact. Four different cyrovials, each loaded with separate reagents and sealed tightly with cap assemblies, were used in the examples demonstrated below. A simple homemade pressure manifold following the design described in detail by Bong et al. (see *Lab Chip*, 11, 743-747) provided independent pressure control for each of the four cryovials with a range from 0-10 psi. A pressure gauge was added to each line for independent monitoring.

Images and movies of droplet dynamics within the microfluidic devices were recorded using a homemade microscope and custom stroboscopic illumination. The microscope consisted primarily of a 10× objective (CFI LU PLAN EPI 10X, Nikon), a tube lens (AC254-200-A, ThorLabs), a camera (Guppy F-046, Allied Vision Technologies), and miscellaneous opto-mechanical hardware for assembly and focusing. A discrete LED for backside sample illumination was aligned along the optical axis of the objective. An electronic circuit of custom design synchronized a short 20 µs strobe of the LED with the longer exposure of the camera, enabling high speed imaging of the droplets. Without strobed illumination the droplets would otherwise appear as streaks in the images due to the long minimum exposure times that are common for inexpensive cameras. The camera was interfaced to a personal computer via FireWire supported by the camera and commercial frame grabbing software (VIMBA SDK, Allied Vision Technologies).

One consequence of the strobed illumination used here combined with the relatively low 16 Hz frame rate of the camera, under typical operating conditions only one image was possible for each droplet. During the time in between frames the droplets from one image would move out of the field of view, being replaced by new ones for the next image. Nevertheless quite high quality videography of droplet dynamics was obtained by taking advantage of the very stable flow rates from using fixed pressure to drive the flow. High flow rate stability translated into very uniform droplet generation rates. The technique used to deliver pseudo-high speed videography here was to tune droplet generation or merge rates such that the characteristic droplet frequency was an integer multiple of the frame rate of the camera, and then offset by just a little. If the relative frequencies were in perfect phase with each other, then one droplet would be replaced by others at the identical position in successive images. This condition was easy to achieve in practice, and the videos appeared as still images attesting not only to the stable generation/merge rates but also indicating a high uniformity in droplet sizes as a result of stable flow (data not shown). When the flow rates were adjusted slightly to add a small phase shift between the droplet frequency and the frame rate, each successive set of droplets would appear displaced a small distance in the image frame resulting in the appearance of slow motion. This approach is termed pseudo-high speed videography herein.

Droplet Generation

Figure 18:
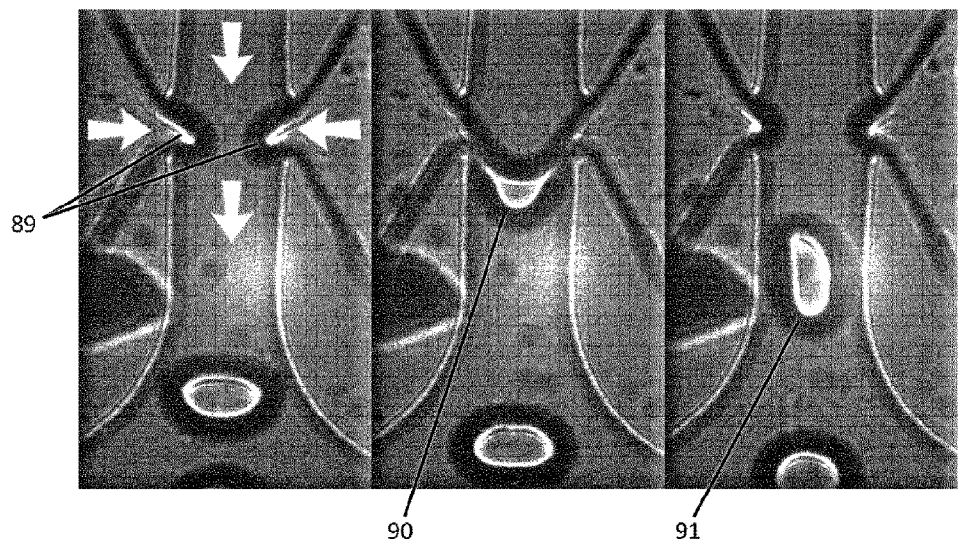
FIG. 18 shows droplet generation within a microfluidic chip.

FIG. 18 shows droplet generation using the microfluidic device in FIG. 16 and instrumentation as described above. The three panels in FIG. 18 show pseudo-sequential events during the three main steps in droplet generation. As described above, the stroboscopic illumination method is an inexpensive alternative to high speed videography known well to those of ordinary skill in the art and widely accepted for characterizing droplet dynamics. For clarity, from this point forward the events in droplet generation will be described as if the successive images captured the dynamics of an individual droplet before, during, and after creation. It is understood that the actual images show different droplets during these stages, but that the dynamics for an individual droplet are reasonably expected to be identical. Arrows in the first panel of FIG. 18 indicate the direction of flow. A continuous oil phase arrived at the fluidic intersection from the channel at the top in FIG. 18, and two different continuous aqueous phases were driven into the intersection from left and the right. A mixed phase flow containing discrete aqueous droplets dispersed in a continuous phase emerged from the intersection toward the bottom of FIG. 18.

In the first step in droplet generation, two boluses of liquid 89 emerged from the left and the right channels in FIG. 18. Fluidic strain from the oil phase distorted the shape of these boluses as they emerged, however they did not snap off before the two boluses contacted and merged 90. The application of an electrical field between the two boluses facilitated the merge, as described in detail below. Lastly, once the merged bolus grew to a threshold size it snapped off from both left and right channels, under the fluidic strain from the oil, yielding a discrete droplet 91. This process repeated continuously generating a steady stream of uniformly sized aqueous droplets.

A modest voltage was applied across the left and the right channels for three different purposes using the circuit described above (see also, FIG. 14). The aqueous phase contained 10 mM Tris buffer at pH 8.0, 1 mM EDTA, and 50 mM NaCl, and hence had ample electrical conductivity to carry current through the microfluidic device at modest voltages as described in the resistor model of the microfluidic circuit above. The first purpose of the electrical field was to enable contact between the two boluses of aqueous fluid emerging into the intersection of the generation. Without the electrical field the two boluses generally did not make contact under those flow rate conditions that were otherwise suitable for droplet generation when the field was applied. Rather the left and right channels in FIG. 18 spontaneously operated as two independent 'T'-shaped droplet generators, but alternating with each other: first one would generate a droplet, then the other, and back to the first again. Without wishing to be bound by any theory, it is expected that concurrent droplet generation in devices similar to the droplet generator here will spontaneously adopt interleaved droplet generation because that condition minimizes the peak pressure within the intersection. Hence a primary purpose for applying an electrical field between the two boluses of liquid is to overcome spontaneous interleaving by providing an attractive electrical force between the two boluses. During electrical field-induced merging the insulating gap between the two emerging boluses of liquid (89 in FIG. 18) energizes like a parallel plate capacitor: current flows into the device from the externally applied voltage resulting in charge accumulation at the two surfaces. One surface becomes increasingly positively charged and the other becomes negatively charged. Charge accumulates until the voltage across the insulating gap offsets the supply voltage. The positive charges at one surface and the negative charges at the other surface experience Coulombic attraction, producing an attractive force between the two surfaces that can overcome the spontaneous tendency of self-avoidance through interleaved operation. The device in this example required ~10 V to overcome interleaved operation, however hysteresis was observed in operation. Once the merge was established it could be maintained at lower voltages down to ~4 V. Reducing the voltage below that threshold value reverted droplet generation to interleaving, and then the full 10 V was required again to recover merge functioning. Without wishing to be bound by any theory, the hysteresis can be understood as a requirement of extra energy to synchronize the system. However, once synchronized less energy is required to maintain steady operation.

As described above, a second purpose for the electrical field is to punch through any surfactant layer that hinders the approach of the two aqueous interfaces. In the example here, the dominant effect otherwise preventing successful merging was interleaved flow. All applied voltages that overcame interleaving were also sufficient to induce the merge. Hence while the impact of surfactant stabilization was not directly observed in this example, it is presumed that the charge accumulation at the surfaces that overcame interleaving was also sufficient for boundary destabilization.

Figure 19:
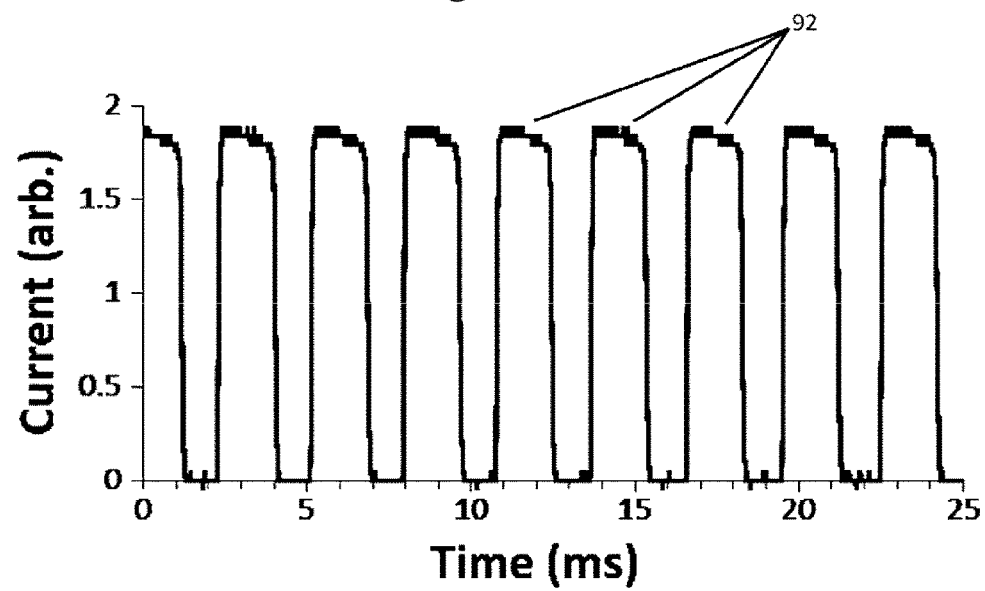
FIG. 19 shows electronic detection of the generation of microdroplets.

A third purpose for the electrical field was to provide an electrical method of droplet measurement. FIG. 19 shows the electrical current flowing through the microfluidic device in FIG. 16 during droplet generation under conditions similar those for FIG. 18. The electrical current was measured by the electrical circuit described above (see also FIG. 15). Periodic bursts of current 92 were recorded on a digital storage oscilloscope coinciding with the formation of an electrolyte bridge 90 during droplet generation. To confirm this interpretation of the electrical signal, the microfluidic system was driven at very low droplet generation frequencies below the camera frame rate allowing the dynamics of individual droplets to be observed before, during, and after bridge formation, meanwhile correlating these events with the electrical measurement. At higher generation frequencies the time resolution of the imaging system was insufficient to track individual droplets. Nevertheless, the measured frequency by the electrical approach also coincided with expectations from the vision system. The stroboscopic videography showed apparently motionless videos whenever the droplets were generated at frequencies measured by the electrical system to be equal to integer multiple of the video frame rate. Also, these motionless videos only occurred at the integer multiples. The simplest interpretation of the electrical measurement is that each burst of current arises from the formation of an electrolyte bridge across the microfluidic intersection in the droplet generator. Since there is one bridge formed per droplet generated, the electrical measurement provides a direct observation of droplet generation that was used here for frequency measurements and droplet counting. For example, in the plot shown in FIG. 19 eight complete droplet generation events were recorded spanning a time of ~23 ms, translating to a droplet generation frequency of ~350 Hz.

The drive pressures for this example ranged from 3-8 psi depending on the condition of the chip, the target operating frequency, and the desired droplet size. Generally higher pressure on the oil line favored smaller droplets at higher frequency due to increased fluidic strain in the intersection, and higher aqueous flow rates favored larger droplets. Thus it was possible to tune the droplet size and generation frequency by varying the oil and aqueous flow rates. It was also possible to vary the relative flow rates of the aqueous phases to yield different droplet compositions.

The oil phase used here and throughout the examples contained 73% Tegosoft DEC (Evonik), 20% mineral oil, and 7% ABIL WE (Evonik) according to the formulation from Schütze and Glökler (see *Lab Times*, 1, 50, 2011). This oil is referred to as ID oil throughout.

Droplet Merging

Figure 20:
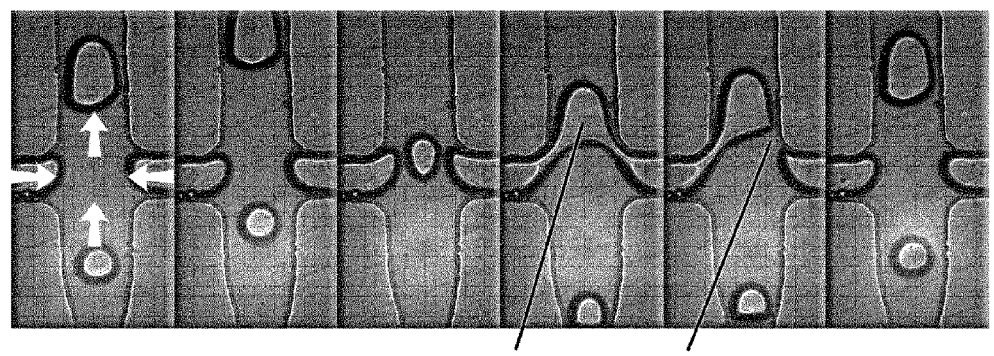
FIG. 20 shows droplet merging within a microfluidic chip.

FIG. 20 shows droplet merging using the bi-injector microfluidic device in FIG. 17 and instrumentation as described above. Arrows in the leftmost panel indicate the direction of flow, and the six panels show pseudo-sequential events during the three main steps in droplet merging as follows. First, a dispersed aqueous droplet isolated within a continuous oil phase arrived at the bi-injector intersection from the bottom channel (three leftmost panels in FIG. 20). Simultaneously, two boluses of liquid emerged from the injector channels (left and right channels in FIG. 20) into the intersection and merged with the incoming droplet forming a transient bridge 93 between the two aqueous injectors. Shortly thereafter fluid strain overcame surface tension and the combined bolus snapped off 94 from the aqueous injectors yielding a larger droplet (rightmost panel) that contained all of the contents of the original droplet plus extra injected fluid volume from the left and right channels.

Not shown in FIG. 20, upstream from the bi-injector an 'X'-shaped microfluidic component was run as a droplet generator, supplying both the oil and the dispersed droplets to the bi-injector. The size and the frequency of the droplets supplied to the bi-injector was controlled by varying the flow rates of the aqueous and oil phases according to guidelines well understood by those of ordinary skill in the art. The flow rates of the aqueous injectors were poised such that each droplet arriving at the bi-injector intersection encountered and merged with two protruding boluses of injector fluid.

It was possible to set the flow rate from the injectors lower such that not every incoming droplet would encounter injection fluid (data not shown). In this operating mode, droplet merging would alternate between merged and unmerged droplets since each droplet that "skipped" the injection fluid would be followed immediately by another that could not skip past because the injection boluses would have extended further into the intersection in the meantime. The transition between merging and skipping was quite sharp. It was difficult to maintain the system at the transition point in between the two modes—characterized by random vacillations between merging and skipping—within the normal variation of flow rates. The transition was also very recognizable as an abrupt 2× drop in merge frequency using the electrical measurement described below. Higher order skipping is possible by further decreasing the injector flow rates or increasing the droplet arrival rate.

On the other hand, if the flow rate from the injectors is set too high relative to the droplet arrival rate then the opposite phenomenon occurs: the injector fluids encounter each other first forming a merged bolus that snaps off before the intended droplet arrives. In this "overshooting" mode of operation the injector functions half time as a simple generator like in the example above, and the other half as a merge device. This operating mode was also discernible by electrical detection: the duration of the fluidic bridge between injectors varied depending on the presence of a target droplet, resulting in alternating bursts of current with different widths (data not shown). Of course there are other possible modes of operation from varying flow rates, for example asymmetric injection with a higher flow in one injector than the other. The invention considers any operation that leads to a transient fluidic bridge spanning the bi-injector intersection, however the most straightforward operation is the one-to-one injection shown in FIG. 20. There was a sizeable window of flow conditions for one-to-one injection between the skipping and overshooting modes that allowed the merged droplets to be formulated with significantly different fractions of fluid from the three aqueous sources. Thus the bi-injector device is both stable with regards to droplet dynamics but also flexible in operation to accommodate varying formulations.

In this example, the oil and all of the aqueous phases were the same as above for droplet generation. Typical operating voltages ranged between 10-20 V. Pressures ranging from 2-8 psi were used to drive flow.

Figure 21:
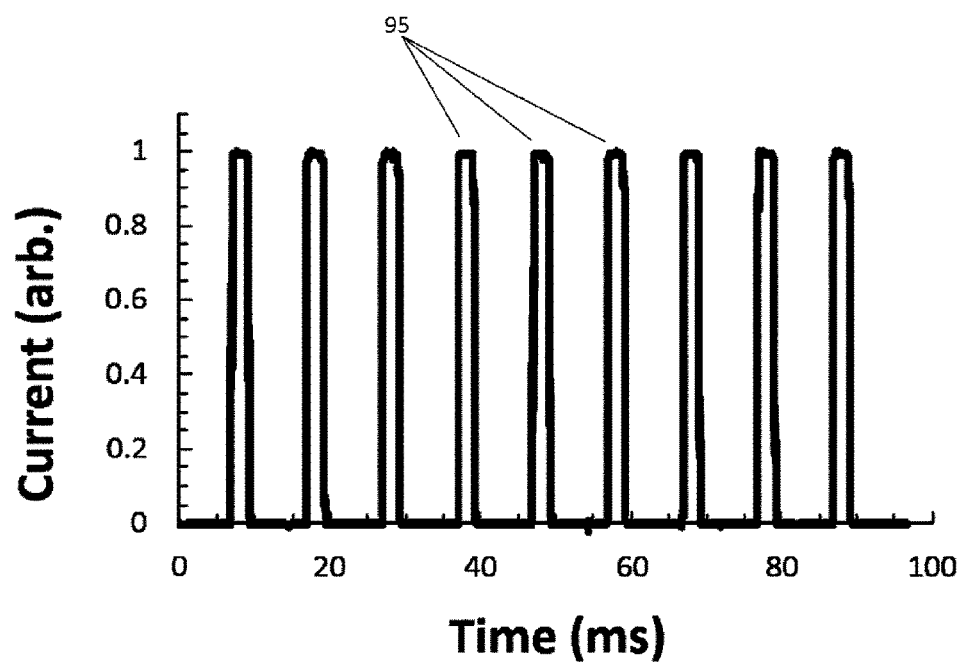
FIG. 21 shows electronic detection of microdroplets merging.

FIG. 21 shows the electrical measurement performed in the same manner as above for droplet generation. Clearly discernible bursts of current 95 coincided with droplet merge events allowing a direct measurement of merge activity within the microfluidic device that was independent of the vision system. As before, strobed illumination was used to identify those merge frequencies—as measured by the electrical system—that coincided with apparently motionless video. Again these frequencies were integer multiples of the video frame rate, confirming the interpretation of the current bursts as arising from merge events. As with droplet generation above, the electrical signature from merging droplets can reveal droplet merge frequency, droplet counts, "skipping" and "overshooting" modes as described above, the relative aqueous vs. oil fractions from the duty cycle, incoming droplet volumes from flow rate÷frequency, and other performance parameters. The invention in not limited with regard to the type of information that the electronic signature can reveal.

Microparticle Synthesis and DNA Entrapment

As a non-limiting example of the flexibility of the bi-injector for performing complicated biochemical reactions, the bi-injector device in FIG. 17 was used to synthesize hydrogel microparticles that contained covalently bound DNA molecules. These microgels were synthesized within droplets that were formulated using the bi-injector device in FIG. 17 as follows.

The aqueous phase in 85 that is dispersed by the upstream droplet generator contained a mixture of DNA, pH buffer, electrolytes, and surfactant. The DNA was synthesized by PCR amplification of a synthetic ErbB3 gene fragment (gBlock, IDT) with a conventional forward primer (IDT), a reverse primer that contained an Acrydite™ moiety (IDT), PCR master mix (TaqMan Universal Master Mix II, Life Technologies), and supplementary dNTPs (0.2 mM, PCR Nucleotide Mix Plus, Roche) (see Table 1 for nucleic acid sequences) using the following thermal cycling parameters: 10 min, 95° C. hot start with 31 cycles of 1 min, 60° C. then 15 s, 95° C. Gel electrophoresis (E-Gel Go! with 2% agarose gel, Life Technologies) of the amplification product revealed a single band at the expected position, and the concentration of DNA was 2.3 µg/mL measured by quantitative fluorimetry (Qubit 2.0 with dsDNA BR Assay, Life Technologies). Primers were designed with online Primer3 software according to methods well known to those of ordinary skill in the art using a larger section of the ErbB3 gene than the one actually synthesized. Rather, after primer selection the section of the gene actually synthesized was trimmed to span the primers only. The amplified DNA was used without any further purification, and diluted into a buffer for running within the chip. The final composition of the droplets entering the bi-injector, ignoring unconsumed remnants from the PCR mixture, was 0.3 µg/mL DNA, 8.7 mM Tris (pH 8.0), 43 mM NaCl, 2.6 mM $MgCl_2$, and 0.4% Tween-20.

The two reactive halves of the prepolymer mixture, the monomers and the chemical initiator, were separated into the two different injectors 87 and 88, preventing polymerization until after emulsification. The monomer solution contained 12% 19:1 acrylamide/bis-acrylamide, 7 mM Tris (pH 8.0), 35 mM NaCl, 2.1 mM $MgCl_2$, 0.35% Tween-20, and 100 mM ammonium persulfate (APS). The initiator solution contained 200 mM tetramethylethylenediamine (TEMED), 10 mM Tris (pH 8.0), 50 mM NaCl, 3 mM $MgCl_2$, and 0.5% Tween-20. The acrylamide monomers and the APS were combined in one solution yet did not initiate polymerization without the TEMED catalyst. APS and TEMED were separated in this way to prevent any loss of activated initiator function during the extended period of operating the microfluidics. Persulfates are susceptible to electrochemical reduction into sulfates with a redox midpoint potential of 2.1 V. To prevent any unintended consequences of APS reduction at the significantly higher voltages used here, the polarity of the electrical circuit was set such that solution containing APS was protected within the oxidizing environment of the anode instead of the reducing environment at the cathode.

The instrument was loaded with the three aqueous phases above and ID oil, and operated as described for droplet merging above. The flow rates were adjusted by-eye based on the projected droplet area in the images such that equal quantities of each aqueous fluid were merged into the final merged droplet. The nominal resulting reaction mixture contained 4% 19:1 acrylamide/bis-acrylamide, 70 mM TEMED, 30 mM APS, 0.1 µg/mL DNA, 10 mM Tris (pH 8.0), 50 mM NaCl, 3 mM $MgCl_2$, and 0.5% Tween-20. The droplets were merged at a rate of 100 Hz with 20 V applied across the bi-injector and with fluidic drive pressures between 2.5 and 5.0 psi. The droplets were collected for 2 hours and polymerization was allowed to complete for another 2 hours.

~0.5 mL of emulsion was collected, and the emulsion was broken by addition of 0.5 mL each of 1-butanol and an aqueous buffer containing 10 mM Tris (pH 8.0), 1 mM EDTA, and 0.5% Tween-20 (TET buffer). After mixing, the broken emulsion was centrifuged at 200×g for 30 s yielding two distinct phases, including a visible large pellet. The pellet was gently resuspended into the lower phase by pipetting and then the lower phase was aspired and the top phase discarded. The pellet was washed twice in 1 mL of TET, with centrifugation in between, and then resuspended in 0.5 mL of TET. Brief inspection of the purified particles by low power brightfield microscopy revealed a multitude of circular shapes consistent with particles.

As a negative control experiment, the same procedure as above was repeated except without DNA. A small aliquot of each type of particle was intercalated with 1×SYBR Green (Life Technologies), a non-specific fluorescence stain for double stranded DNA. The particles were imaged on an inverted epi-fluorescence microscope (IX81, Olympus) using fluorescence filters (ET480/40× excitation, ET535/50m emission, T510lpxrxt BS dichroic, Chroma) and a high efficiency fluorescence imaging camera (Insight, SPOT Imaging). In the negative control without DNA, the particles were evident under bright field illumination however they were completely invisible by fluorescence imaging. This result confirms that there is no non-specific fluorescence staining of the acrylamide hydrogel itself. In contrast, the particles containing DNA were brightly fluorescent despite washing. The Acrydite™ moiety on the reverse primer is thermally stable and should survive extension of the primers into double stranded PCR amplification products (called amplicons for short). However Acrydite™ is reactive during free radical polymerization—the mechanism of acrylamide gelation—hence the amplicons were expected to become covalently incorporated into the acrylamide hydrogel during polymerization via the Acrydite™ linker. While the evidence presented thus far cannot exclude the possibility that the amplicons were merely entangled within the microgels, the ready accessibility of the DNA to SYBR staining suggests a high degree of mobility within the gel that would also permit DNA diffusion out of the particle. Stronger evidence of covalent coupling is presented in the next example using sequence-specific hybridization to identify the DNA.

Figure 22:
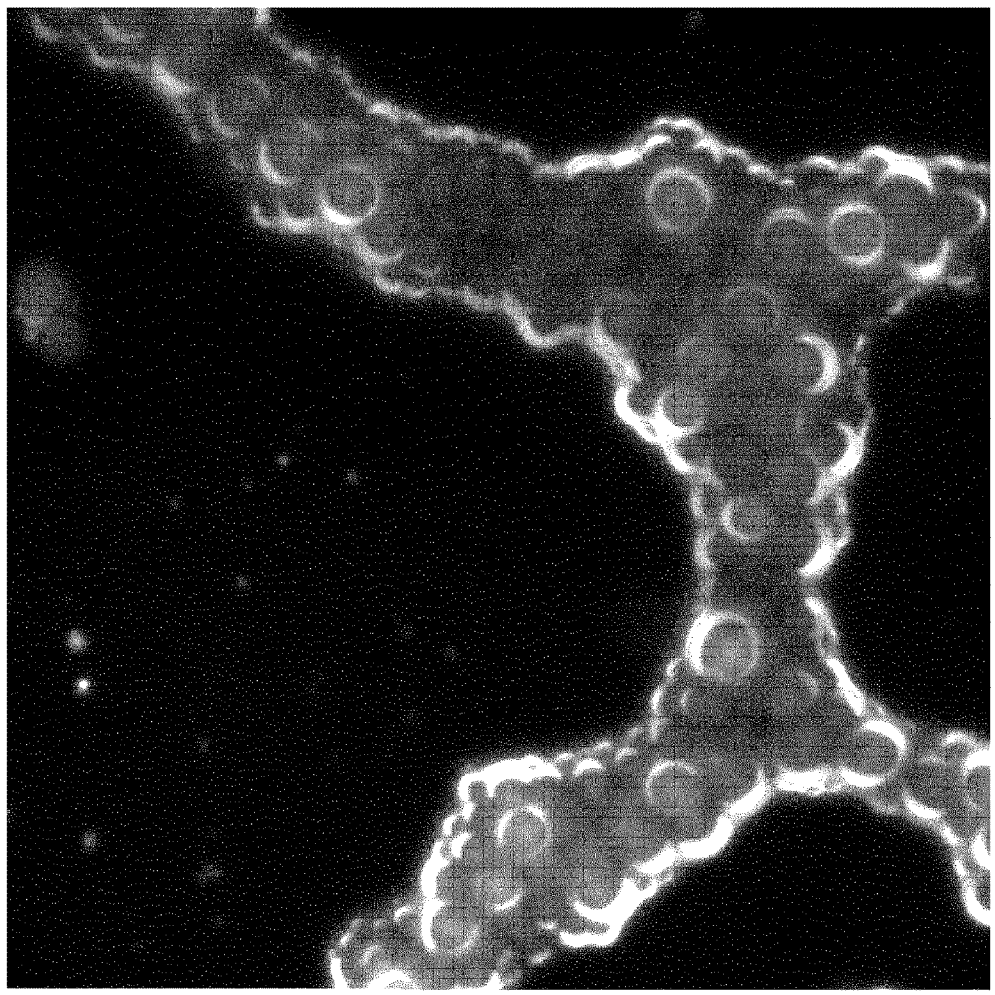
FIG. 22 shows hydrogel microparticles.

To demonstrate that the particles were indeed semi-rigid solids the slide containing DNA particles was allowed to dry out briefly. FIG. 22 shows a fluorescence image of the dried slide. Before drying the particles were monodisperse and scattered randomly across the slide surface. During drying the receding water meniscus carried the particles, ultimately gathering them together into the clumps evident in FIG. 22. If the particles were not semi-rigid, but instead some type of residual mixed phase liquid state that survived washing, then it is highly unlikely that they would have survived completely intact throughout the drying process here.

DNA Genotyping within Hydrogel Microparticles

The sequence of the DNA entrapped in the hydrogel microparticles was identified by fluorescence hybridization. Both types of particles fabricated in the previous example (+/− DNA) were analyzed with two different hybridization probes separately, one with a perfectly matching sequence and the other with negligible sequence similarity. As described in detail below, the probe with the matching sequence successfully identified the DNA contained within the hydrogel. This non-limiting example demonstrates the ability to characterize the sequence of DNA entrapped within hydrogels that were created using the methods of the invention using standard solution-state biochemistry. The amplicons were co-localized within the scaffold of the gel, yet they remained accessible to conventional forms of DNA characterization.

150 μL aliquots of particles for each experimental condition were spun down for 1 min at 200×g and resuspended into 300 μL of hybridization buffer containing 10 mM Tris (pH 8.0), 50 mM NaCl, 3 mM $MgCl_2$, and 0.5% Tween-20. In the next step, the entrapped DNA was prepared for hybridization by melting off and washing out the complementary strand that was not covalently bound to the gel matrix. Only the reverse primer for amplifying the ErbB3 template DNA contained the necessary Acrydite™ moiety for covalent incorporation into the gel matrix. Hence it was expected that only the reverse strand would remain inside the particles after this step. The resuspended particles were incubated twice in a rotary shaker (BioShake IQ, QUANTIFOIL Instruments GmbH) at 90° C. and 1,200 rpm for 30 minutes, washed twice after each incubation with 1 mL of the hybridization buffer and resuspended back into 300 μL.

The particles were then incubated with rotary mixing against 1 μM of probes at 58° C. and 1,200 rpm for two hours. The probes were designed by methods known well to those of ordinary skill in the art and were synthesized by IDT. IDT Biophysics v1.00 and mFold (see Zuker et al., Nucleic Acids Res., 31(13), 3406-3415, 2003) were used to determine the melting temperatures and to avoid secondary structure respectively. After hybridization the particles were washed twice with hot hybridization buffer (58° C.) to avoid non-specific binding and again resuspended in 300 μL of hot hybridization buffer. To remove any unbound probe from within the hydrogel matrix, the particles were then incubated twice with rotary mixing at 58° C. and 1,200 rpm for 30 minutes, followed by two washes with hot hybridization buffer and resuspension into 300 μL hot hybridization buffer afterwards.

Figure 23:
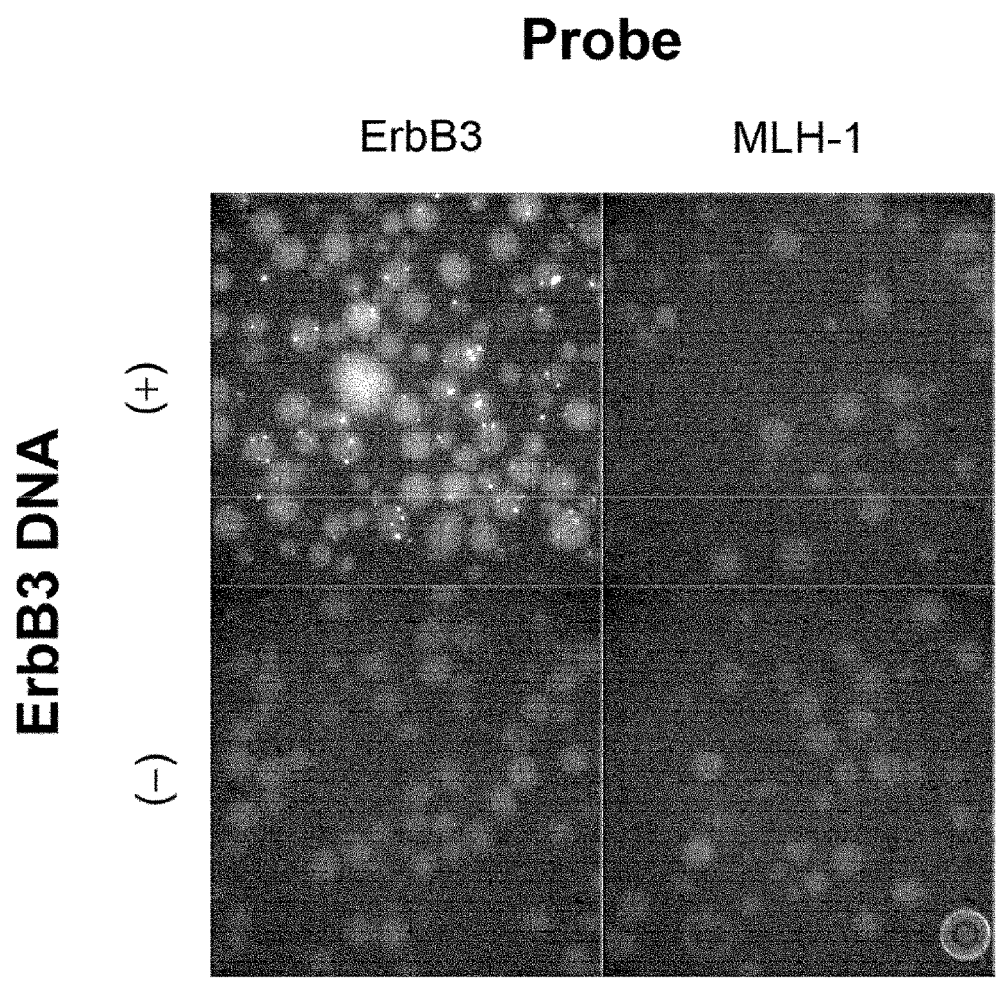

FIG. 23 shows fluorescence images of the four different particle preparations (+/− DNA and ErbB3/MLH-1 probe). Fluorescence microcopy was performed as above and images were captured using the same camera settings for each sample (2 s exposure, gain=1, and 4×4 binning) to allow quantitative comparison. All of the particles exhibited some amount of fluorescence, however the DNA(+) particles probed by the sequence-specific ErbB3 probe were clearly significantly brighter than the others by-eye. Quantitative comparison of the different hybridization reactions was performed by selecting five similarly sized particles from each image in FIG. 23 for fluorescence intensity analysis. Similarly sized particles were selected to avoid any size related artifacts. As discussed in detail below, the selected particles most likely originated from intact and full-sized droplets.

Figure 24:
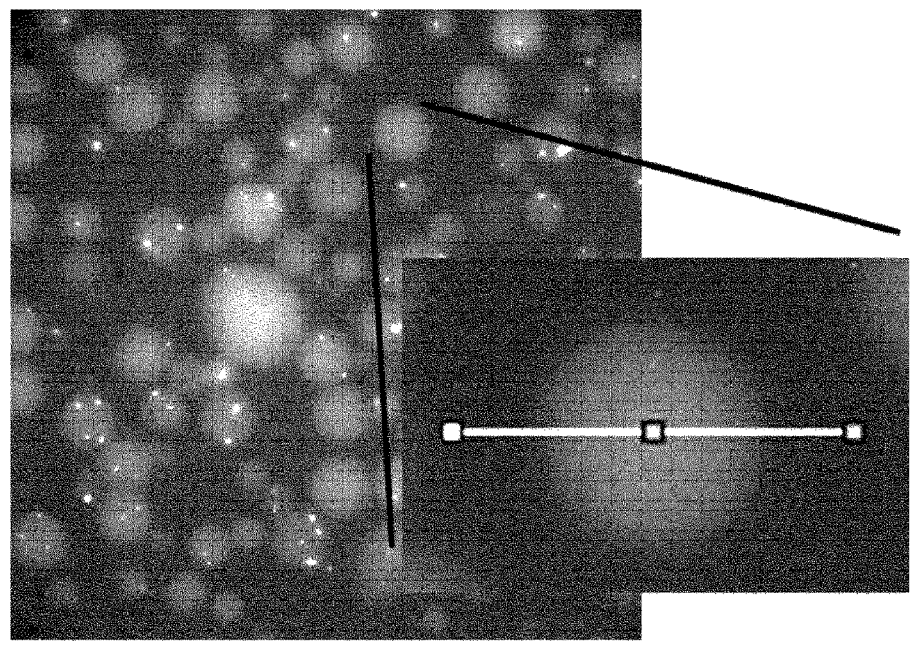
FIG. 24 shows imaging analysis of fluorescent hydrogel microparticles.
Figure 24:
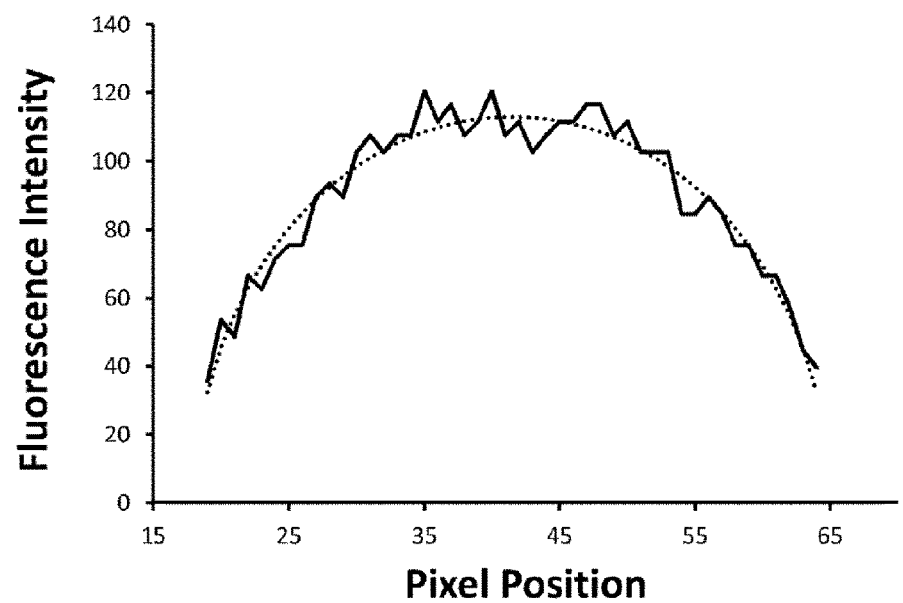
Figure 25:
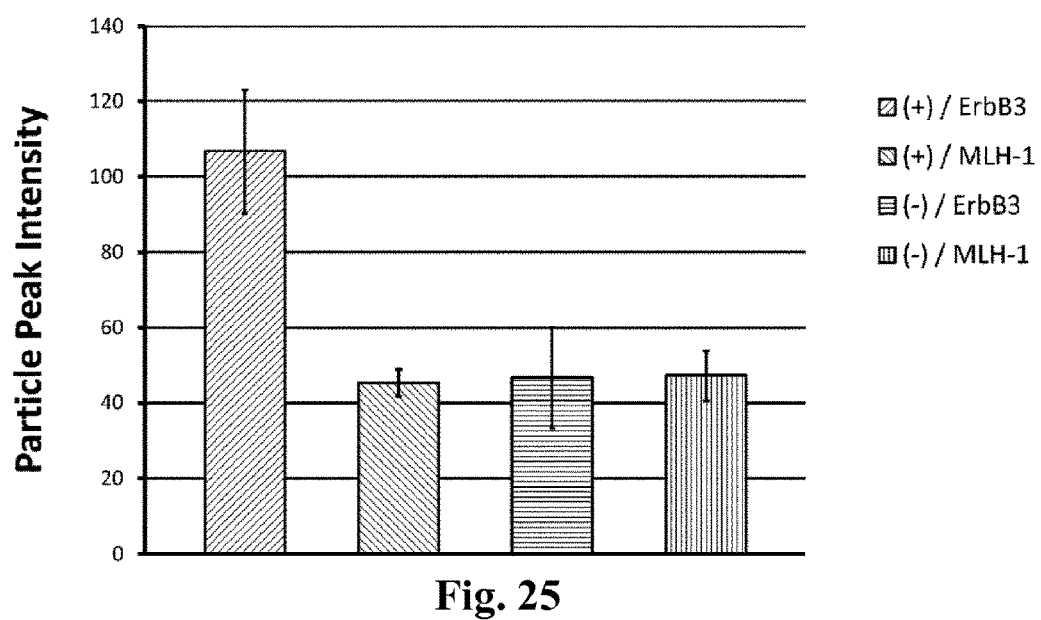
FIG. 25 shows analysis of a DNA genotyping assay.

FIG. 24 shows the selection of a single particle for analysis. The image intensity along a line profile (inset in FIG. 24) was recorded using ImageJ image analysis software (US National Institutes of Health), revealing a parabolic shaped intensity profile with a peak intensity in the middle (solid line in the plot in FIG. 24). The intensity profile yielded an excellent fit (dotted line in the plot in FIG. 24) after baseline subtraction to the Pythagorean function of the form $$f(x) = B\sqrt{1 - \left(\frac{x - x_0}{A}\right)^2}$$

where B is the peak fluorescence intensity, A is the radius of the particle, and $x_0$ is the offset of the center in the x-direction. The baseline was determined from the average of the line profile outside of the particle area. Best fit analysis was performed for each selected particle by a grid search of the A, B, and $x_0$ parameter space using custom software for chi-square minimization. Excellent fits were found for each of the particles analyzed. Values of the peak intensity, B, were averaged for each type of particle and are presented in FIG. 25 where the error bars reflect the standard deviation of B. The peak intensity of the DNA(+) sample with the matching probe was significantly brighter than the others within the experimental uncertainty, and there was no significant non-specific association of the mismatch probe. The intensity of the mismatched probe was not differentiable from the negative control particles without DNA within experimental uncertainty. These results demonstrate sequence-specific identification of the DNA entrapped within hydrogel particles by fluorescence hybridization.

The goodness of fit of the Pythagorean function above is consistent with uniform hybridization throughout the particles. Uniform hybridization predicts that the fluorescence intensity should be a function of the cross section of the spherical particle, a maximum in the middle and dropping to zero at the periphery according to the Pythagorean function. In contrast, for example, if the gel were relatively impermeable to the hybridization probes then most of the fluorescence staining would occur at the surface. In this case the largest cross section of the shell of a sphere occurs at the periphery with a minimum in the middle, predicting an intensity profile with horns on each end. The apparent accessibility of amplicon DNA to hybridization throughout the particles strongly suggests that the amplicons are covalently bound. First, efficient hybridization requires that the complementary strand be removed, and second, it requires that the hybridization probe be relatively free to diffuse throughout the particles. It is quite unlikely that both the complementary strand and the hybridization probes would be freely mobile within the particles, and yet the similarly sized reverse strand would somehow be restricted within the gel. The simplest explanation of the results here is that the reverse strand is covalently bound through the Acrydite™ moiety.

One advantage of droplet-based microfluidics is the high degree of uniformity in droplet sizes typically produced. Indeed, the droplets emerging from the bi-injector here also appeared very uniform in size. However, downstream from the bi-injector near the exit port the channel was partially collapsed due to a simple design defect unrelated to the invention (data not shown). As a consequence some fraction of the merged droplets were shredded into smaller droplets. This distribution of droplet sizes is evident on inspection of the particles in the images in FIG. 23. There is a preponderance of particles of one size—the size selected for intensity analysis here—combined with a wide distribution of smaller sizes and only one particle that was much larger. Furthermore the CV for particle radius, A, was very small for all four particle preparations (2-5%). The simplest interpretation of this distribution of particle sizes is that many of the particles emerged intact from the chip despite the port defect and polymerized into uniformly sized particles. The droplets that were shredded on exiting the chip polymerized into a wide variety of smaller particles. The complete lack of any particles slightly larger than the predominant size is also consistent with this interpretation. Generally larger droplets arise from the coalescence of two or more droplets. Thus an indication of a uniform emulsion is a multimodal distribution of droplet sizes with gaps in between. The lack of droplets that are slightly larger than the predominant size combined with the presence of a very large droplet suggests a multimodal distribution. In conclusion, the variety of particle sizes in this example does not imply any limitation of the invention.

In the example of DNA genotyping shown here, using methods of the invention, the DNA was amplified first, then emulsified into droplets, and finally entrapped within hydrogel microparticles. The invention is not limited to this order of events. For example, those of ordinary skill in the art will appreciate that the DNA may be emulsified first, then amplified, and finally injected into the microfluidic device for hydrogel entrapment. In this case the starting emulsification may also be carried out at limiting dilution as in emulsion PCR. The invention is not limited to either of these orders of events, nor is the DNA sample limited to PCR products. Rather the invention considers broadly any means of delivering nucleic acids of any origin into the microfluidic devices of the invention for entrapment.

Also in the example of DNA genotyping shown here, the microfluidic methods of the invention were used for DNA entrapment. The invention is not limited in this regard. Those of ordinary skill in the art will appreciate that while the microfluidic methods of the invention are well suited for this application, other microfluidic methods may be substituted in a variety of ways. The invention considers any microfluidic method of merging a stream of droplets containing DNA with another stream or streams of fluid, either continuous or dispersed, that contain pre-polymer solution and initiators.

Also in the example of DNA genotyping shown here, the DNA sequence was identified by fluorescence hybridization. The invention is not limited in the regard. Any method of characterizing DNA sequence is considered by the invention.

TABLE 1

| Nucleic Acid Type | Sequence |
|---|---|
| Forward primer | 5'-CCACTCTTCCCTCTGCTTTG-3' |
| Reverse primer | 5'-Acrydite-CACCTCACACCTCTCGTAGA-3' |
| ErbB3 probe | 5'-GCCTGAGTGTGACCGGCGAT-Alexa488-3' |
| MLH-1 probe | 5'-Alexa488-TGCAAAATCCACAAGTATTCAAGTG-3' |
| ErbB3 gene fragment | 5'-CCACTCTTCCCTCTGCTTTGAACAGTGTGTCCTGGG ACTCTGAATGGCCTGAGTGTGACCGGCGATGCTGA GAACCAATACCAGACACTGTACAAGCTCTACGAG AGGTGTGAGGTG-3' |

I claim:

1. A method comprising:
providing a system, the system comprising a substrate that defines microfluidic channels including:
a main channel having a main input in fluid communication with a main output, the main channel defining an intersection site along a path of fluid flow from the main input to the main output;
a first side channel having a first side input in fluid communication with a first side output, the first side output being in fluid communication with the main channel at the intersection site;
a second side channel having a second side input in fluid communication a second side output, the second side output being in fluid communication with the main channel at the intersection site;
a first electrode comprising an electrochemical half-cell in fluidic contact with the first side channel fluid when the first side channel has been charged with the first side channel fluid; and
a second electrode comprising an electrochemical half-cell in fluidic contact with the second side channel fluid when the second side channel has been charged with the second side channel fluid;
charging the main channel with a main channel fluid from the main input;
charging the first side channel with a first side channel fluid from the first side input, the first side channel fluid being immiscible with at least a first component of the main channel fluid;
charging the second side channel with a second side channel fluid from the second side input such that the first and second side channels are separated from one another by the main channel fluid, the second side channel fluid being immiscible with at least the first component of the main channel fluid;
flowing the main channel fluid from the main channel input to the main channel output and through the intersection point;
connecting the first and second side channel fluids with a fluid bridge at the intersection point; and
disconnecting the fluid bridge from at least one of either the first or the second side channel fluids so that the first and second side channel fluids are separated by the first component of the main channel fluid.

2. The method of claim 1 wherein the fluid bridge consists of a second component of the main channel fluid.

3. The method of claim 1 wherein the first and second side channel fluids are miscible with each other.

4. The method of claim 3 wherein the fluid bridge is miscible with both the first and second side channel fluids.

5. The method of claim 1 wherein connecting the first and second side channel fluids with the fluid bridge comprises forming an electrically conductive connection between the first and second side channel fluids.

6. The method of claim 1 wherein the system further comprises a voltage source connected to both the first electrode and the second electrode.

7. The method of claim 1 wherein:
the first electrode is located within the first side channel; and
the second electrode is located within the second side channel.

8. The method of claim 1 wherein the first side channel fluid, the second side channel fluid and the fluid bridge are all aqueous.

9. The method of claim 1 wherein the first component of the main channel fluid is an oil.

10. The method of claim 1 wherein the fluid bridge consists essentially of the first and second side channel fluids, and contains substantially none of the first component of the main channel fluid.

11. The method of claim 10 wherein connecting the first and second side channel fluids with a fluid bridge comprises extending the first and second side channel fluids into the intersection site so that the first and second fluids come into contact, thereby forming the fluid bridge.

12. The method of claim 11 wherein disconnecting the fluid bridge from the first and second side channel fluids comprises separating the fluid bridge from both the first and second side channel fluids thereby creating a droplet consisting essentially of the first and second side channel fluids.

13. The method of claim 12 further comprising
encapsulating a species within the fluid droplet; then
injecting into the fluid droplet reactants for gel polymerization; then
rigidifying the droplet by gel polymerization; and
capturing the species within the rigidified droplet during polymerization.

14. The method of claim 13 wherein injecting comprises microfluidic injection, picoinjection or lambda injection.

15. The method of claim 13 wherein the species includes a nucleic acid.

16. The method of claim 15 wherein the nucleic acid is clonal.

17. The method of claim 16 wherein the clonal nucleic acid arose from:
encapsulating a single DNA molecule within a droplet; and then
amplifying the DNA within the droplet.

18. The methods of claim 15 further comprising characterizing the nucleic acid.

19. The method of claim 18 wherein characterizing comprises sequencing the nucleic acid.

20. The method of claim 19 further comprising identifying and quantifying genotypes based on the characterization of the nucleic acid.

21. The method of claim 19 further comprising sorting the rigidified droplet based on the characterization of the nucleic acid.

22. The method of claim 21 further comprising characterizing the sorted droplets.

23. The method of claim 22 wherein characterizing the sorted droplets comprises sequencing the nucleic acid.

24. The method of claim 23 further comprising identifying and quantifying genotypes based on the characterization of the nucleic acid.

25. The method of claim 15 wherein the nucleic acid is DNA arising from amplification with one or more primers containing a functional group for covalent incorporation into the gel matrix via free radical chemistry during gel polymerization.

26. The method of claim 25 wherein the functional group is a 5' acrydite.

27. The method of claim 13 wherein the nucleic acid is DNA is amplified with one or more primers that either leave an overhang after DNA extension or are cleaved into an overhang.

28. The method of claim 27 wherein the primer comprises a target binding region and an overhang region, and where the overhang region comprises nucleic acid analogs.

29. The method of claim 28 wherein the nucleic acid analogs are LNAs or PNAs.

30. The method of claim 27 wherein the DNA is amplified with one or more tripartite primers comprising a 3' target binding region, a 5' attachment region that forms an overhang during polymerization, and a non-replicable region in between that blocks the polymerase from extending the overhang.

31. The method of claim 27 wherein the DNA concatemerizes at room temperature, with or without unions and blocks, and with or without restriction digestion and ligation, entrapping the DNA within the gel droplet.

32. The method of claim 13 wherein the species is a cell.

33. The method of claim 12 further comprising
injecting into the droplet a bead attached to a hybridization capture agent complementary to a predetermined nucleic acid sequence, the droplet containing amplified DNA; and
capturing the amplified DNA to the hybridization capture agent.

34. The method of claim 33 further comprising characterizing the captured DNA.

35. The method of claim 34 wherein characterizing comprises sequencing the DNA.

36. The method of claim 35 further comprising identifying and quantifying genotypes based on the characterization of the nucleic acid.

37. The method of claim 12 wherein the disconnected fluid bridge contains a species and reactants for gel polymerization, the method further comprising entrapping the species within a gel in the droplet by gel polymerization of the reactants.

38. The method of claim 37 wherein the species is at least one of (a) a nucleic acid, and (b) a cell.

39. The method of claim 10 wherein:
the system further comprises a current meter operably connected to the first and second electrodes so as to be capable of measuring the current between the first and second electrodes as a function of time; and
the method further comprises recording the current measured by the current meter as a function of time.

40. The method of claim 1 wherein the fluid bridge is miscible with the first side channel fluid, or the second side channel fluid, or both.

41. The method of claim 1 wherein the fluid bridge is immiscible with the first side channel fluid.

42. The method of claim 41 wherein the fluid bridge is immiscible with the second side channel fluid.

43. The method of claim 1 wherein:
the fluid bridge is a second component of the main channel fluid; and
flowing the main channel fluid comprises flowing the fluid bridge from the main channel input to the intersection point and from the intersection point to the main channel output.

44. The method of claim 43 wherein:
the system further comprises a current meter operably connected to the first and second electrodes so as to be capable of measuring the current between the first and second electrodes as a function of time; and
the method further comprises recording the current measured by the current meter as a function of time.

45. The method of claim 1 wherein:
connecting the first and second side channel fluids with the fluid bridge comprises incorporating at least some of the first and/or second side channel fluids into the fluid bridge; and
disconnecting the fluid bridge comprises retaining in the fluid bridge the incorporated at least some of the first and/or second side channel fluids.

46. The method of claim 1 wherein disconnecting the fluid bridge comprises:
disconnecting the fluid bridge from the second side channel fluid; and
maintaining contact between the fluid bridge and the first side channel fluid.

47. The method of claim 46 further comprising flowing the fluid bridge from the main channel into the first side channel.

48. The method of claim 1 wherein the system further comprises:
a first pressure source in fluid communication with the first side input, the first pressure source configured so that if the first side channel is charged with a first side fluid, the first pressure source is capable of generating or maintaining within the first side channel fluid a positive pressure, or a negative pressure, or zero pressure with respect to the pressure of the main channel fluid at the intersection site; and a second pressure source in fluid communication with the second side input, the second pressure source configured so that if the second side channel is charged with a second side fluid, the second pressure source is capable of generating or maintaining within the second side channel fluid a positive pressure, or a negative pressure, or zero pressure with respect to the pressure of the main channel fluid at the intersection site.

49. The method of claim 48 wherein:

the second side channel defines (a) a second side current channel and (b) a second side pressure channel;

the second side current channel and the second side pressure channel are both in fluid communication with the input port;

the second side current channel and the second side pressure channel are contiguous at a second side intersection point in the second side channel;

the second side electrode is positioned within the second side current channel; and the second pressure source is positioned in the second side pressure channel.

50. The method of claim 49 wherein the fluid flow path from the second side intersection point to the second side electrode is substantially different in length, cross-sectional area, or both length and cross-sectional area than the fluid flow path from the second side intersection point to the second pressure source.

51. The method of claim 49 wherein the fluid flow path from the second side intersection point to the second side electrode is substantially similar to the fluid flow path from the second side intersection point to the second pressure source.

52. The method of claim 1 wherein the second side channel includes a third side input in fluid communication with the second side output.

53. The method of claim 52 further comprising charging the second side channel with a third side channel fluid from the third side input.

54. The method of claim 1 wherein the first side channel fluid includes a bead attached to a hybridization capture agent complementary to a predetermined nucleic acid sequence.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Homo sapiens

<400> SEQUENCE: 1
ccactcttcc ctctgctttg                                              20

<210> SEQ ID NO 2
<211> LENGTH: 20
<212> TYPE: DNA
<213> ORGANISM: Homo sapiens

<400> SEQUENCE: 2
cacctcacac ctctcgtaga                                              20

<210> SEQ ID NO 3
<211> LENGTH: 20
<212> TYPE: DNA
<213> ORGANISM: Homo sapiens
```

-continued

```
<400> SEQUENCE: 3
gcctgagtgt gaccggcgat                                                       20

<210> SEQ ID NO 4
<211> LENGTH: 25
<212> TYPE: DNA
<213> ORGANISM: Homo sapiens

<400> SEQUENCE: 4
tgcaaaatcc acaagtattc aagtg                                                 25

<210> SEQ ID NO 5
<211> LENGTH: 117
<212> TYPE: DNA
<213> ORGANISM: Homo sapiens

<400> SEQUENCE: 5
ccactcttcc ctctgctttg aacagtgtgt cctgggactc tgaatggcct gagtgtgacc           60
ggcgatgctg agaaccaata ccagacactg tacaagctct acgagaggtg tgaggtg            117
```